US010610423B2

(12) United States Patent
Grenier et al.

(10) Patent No.: US 10,610,423 B2
(45) Date of Patent: Apr. 7, 2020

(54) ABSORBENT ARTICLE COMPRISING A TOPSHEET/ACQUISITION WEB LAMINATE

(71) Applicant: The Procter & Gamble Company, Cincinnati, OH (US)

(72) Inventors: Adrien Grenier, Schwalbach am Taunus (DE); Rodrigo Rosati, Schwalbach am Taunus (DE); Silke Kramkowski, Schwalbach am Taunus (DE); Adele Bruell, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 505 days.

(21) Appl. No.: 15/442,998

(22) Filed: Feb. 27, 2017

(65) Prior Publication Data

US 2017/0258646 A1 Sep. 14, 2017

(30) Foreign Application Priority Data

Mar. 8, 2016 (EP) .................................... 16159086

(51) Int. Cl.
*A61F 13/537* (2006.01)
*A61F 13/512* (2006.01)
(Continued)

(52) U.S. Cl.
CPC ...... *A61F 13/53747* (2013.01); *A61F 13/512* (2013.01); *A61F 13/5123* (2013.01);
(Continued)

(58) Field of Classification Search
CPC .............. A61F 13/51104; A61F 13/512; A61F 13/5123; A61F 2013/51038; A61F 2013/51178
See application file for complete search history.

(56) References Cited

U.S. PATENT DOCUMENTS

| 4,323,068 A | 4/1982 | Aziz |
| 4,846,821 A | 7/1989 | Lyons |

(Continued)

FOREIGN PATENT DOCUMENTS

| CA | 2518857 | 11/2004 |
| EP | 1283028 | 2/2003 |

(Continued)

OTHER PUBLICATIONS

All Office Actions for U.S. Appl. No. 14/844,018.
(Continued)

*Primary Examiner* — Susan S Su
(74) *Attorney, Agent, or Firm* — George H Leal; Christian M Best

(57) ABSTRACT

An absorbent article for personal hygiene comprises a longitudinal axis, a transversal axis perpendicular to the longitudinal axis, a topsheet/acquisition web laminate, a liquid impermeable backsheet, and an absorbent core. The absorbent core is located between the topsheet/acquisition web laminate and the backsheet. The topsheet/acquisition web laminate comprises a liquid permeable topsheet and an acquisition web in a face to face relationship. The topsheet/acquisition web laminate comprises three-dimensional protrusions extending from a plane of the topsheet/acquisition web laminate. The acquisition web is a nonwoven fibrous web comprising an upper layer facing towards the topsheet and a lower layer facing towards the absorbent core. The average diameter of the fibers in the upper layer is higher than the average diameter of the fibers in the lower layer.

20 Claims, 9 Drawing Sheets

(51) Int. Cl.
*A61F 13/511* (2006.01)
*A61F 13/51* (2006.01)
*A61F 13/53* (2006.01)

(52) U.S. Cl.
CPC ............ *A61F 13/51104* (2013.01); *A61F 2013/51038* (2013.01); *A61F 2013/5307* (2013.01); *A61F 2013/530481* (2013.01)

(56) References Cited

U.S. PATENT DOCUMENTS

| | | | |
|---|---|---|---|
| 5,518,801 | A | 5/1996 | Chappell et al. |
| 5,599,335 | A | 2/1997 | Goldman et al. |
| 5,628,097 | A | 5/1997 | Benson et al. |
| 5,804,021 | A | 9/1998 | Abuto et al. |
| 5,888,607 | A | 3/1999 | Seth et al. |
| 5,938,650 | A | 8/1999 | Baer et al. |
| 6,060,638 | A * | 5/2000 | Paul .................. A61F 13/15203 604/378 |
| 6,136,124 | A | 10/2000 | Wagner |
| 6,228,462 | B1 | 5/2001 | Yee et al. |
| 6,274,218 | B1 | 8/2001 | Shimizu |
| 6,344,102 | B1 | 2/2002 | Wagner |
| 6,395,957 | B1 | 5/2002 | Chen et al. |
| 6,440,564 | B1 | 8/2002 | Mclain et al. |
| 6,455,753 | B1 * | 9/2002 | Glaug ............... A61F 13/53717 604/368 |
| 6,610,904 | B1 | 8/2003 | Thomas |
| 6,641,902 | B1 | 11/2003 | Kobayashi et al. |
| 6,685,686 | B2 | 2/2004 | Hermansson et al. |
| 6,700,036 | B2 | 3/2004 | Thomas et al. |
| 6,733,626 | B2 | 5/2004 | Ruthven et al. |
| 6,739,024 | B1 | 5/2004 | Wagner |
| 6,818,802 | B2 | 11/2004 | Takai et al. |
| 6,887,349 | B2 | 5/2005 | Ruthven et al. |
| 7,037,406 | B2 | 5/2006 | Kershaw et al. |
| 7,060,344 | B2 | 6/2006 | Pourdeyhimi et al. |
| 7,172,801 | B2 | 2/2007 | Hoying et al. |
| 7,182,838 | B2 | 2/2007 | Ruthven et al. |
| 7,267,860 | B2 | 9/2007 | Toyoshima et al. |
| 7,294,231 | B2 | 11/2007 | Kershaw et al. |
| 7,297,226 | B2 | 11/2007 | Schulz |
| 7,326,322 | B2 | 2/2008 | Ruthven et al. |
| 7,410,683 | B2 | 8/2008 | Gray et al. |
| 7,468,114 | B2 | 12/2008 | Sato et al. |
| 7,531,062 | B2 | 5/2009 | Kershaw et al. |
| 7,553,532 | B2 | 6/2009 | Gray et al. |
| 7,648,752 | B2 | 1/2010 | Gray et al. |
| 7,678,034 | B2 | 3/2010 | Wilhelm |
| 7,682,686 | B2 | 3/2010 | Gray et al. |
| 7,687,679 | B2 | 3/2010 | Mishima |
| 7,799,176 | B2 | 9/2010 | Wilhelm |
| 7,842,849 | B2 | 11/2010 | Datta |
| 7,857,941 | B2 | 12/2010 | Ruthven et al. |
| 7,951,127 | B2 | 5/2011 | Sanabria et al. |
| 8,142,617 | B2 | 3/2012 | Ruthven et al. |
| D662,326 | S | 6/2012 | Shanbhag et al. |
| 8,231,377 | B2 | 7/2012 | Wittner et al. |
| 8,241,543 | B2 | 8/2012 | O'Donnell et al. |
| 8,287,694 | B2 | 10/2012 | Schulz |
| 8,304,600 | B2 | 11/2012 | Noda et al. |
| 8,313,473 | B2 | 11/2012 | Nada |
| D672,152 | S | 12/2012 | Shanbhag et al. |
| 8,393,374 | B2 | 3/2013 | Sato et al. |
| 8,535,481 | B2 | 9/2013 | Schulz |
| 8,574,209 | B2 | 11/2013 | Nishitani et al. |
| 8,585,958 | B2 | 11/2013 | Gray et al. |
| 8,617,449 | B2 | 12/2013 | Baker et al. |
| 9,108,355 | B2 | 8/2015 | Kume et al. |
| 2002/0004654 | A1 * | 1/2002 | Daniels ............... A61F 13/511 604/380 |
| 2003/0195487 | A1 | 10/2003 | Thomas |
| 2003/0211802 | A1 | 11/2003 | Keck et al. |
| 2004/0002688 | A1 | 1/2004 | Thomas et al. |
| 2004/0140047 | A1 | 7/2004 | Sato et al. |
| 2004/0176733 | A1 * | 9/2004 | Glaug .................. A61F 13/534 604/378 |
| 2004/0229008 | A1 * | 11/2004 | Hoying ............ A61F 13/15707 428/92 |
| 2004/0265534 | A1 | 12/2004 | Curro et al. |
| 2005/0008825 | A1 | 1/2005 | Casey et al. |
| 2005/0281976 | A1 | 12/2005 | Curro et al. |
| 2006/0020250 | A1 * | 1/2006 | Chester ............. A61F 13/53747 604/378 |
| 2006/0111684 | A1 | 5/2006 | Berba et al. |
| 2006/0194027 | A1 | 8/2006 | Pourdeyhimi et al. |
| 2006/0286343 | A1 | 12/2006 | Gray et al. |
| 2007/0073254 | A1 * | 3/2007 | Ponomarenko ....... A61F 13/495 604/383 |
| 2007/0212966 | A1 | 9/2007 | Wittner et al. |
| 2008/0221538 | A1 | 9/2008 | Zhao et al. |
| 2008/0227356 | A1 | 9/2008 | Poruthoor et al. |
| 2009/0030390 | A1 | 1/2009 | Hammons et al. |
| 2010/0028621 | A1 | 2/2010 | Byrne et al. |
| 2010/0035014 | A1 | 2/2010 | Hammons et al. |
| 2010/0036338 | A1 | 2/2010 | Hammons et al. |
| 2010/0209664 | A1 | 8/2010 | Sato |
| 2010/0233438 | A1 | 9/2010 | Stone |
| 2010/0247844 | A1 | 9/2010 | Curro et al. |
| 2010/0249740 | A1 | 9/2010 | Miyamoto et al. |
| 2010/0297377 | A1 | 11/2010 | Buscher et al. |
| 2010/0310810 | A1 | 12/2010 | Bond et al. |
| 2011/0073513 | A1 | 3/2011 | Weisman et al. |
| 2011/0094669 | A1 | 4/2011 | Oetjen |
| 2011/0125120 | A1 | 5/2011 | Nishitani et al. |
| 2011/0260371 | A1 | 10/2011 | Arora et al. |
| 2012/0059343 | A1 | 3/2012 | Kume et al. |
| 2012/0064280 | A1 | 3/2012 | Hammons et al. |
| 2012/0064298 | A1 | 3/2012 | Curro et al. |
| 2012/0136329 | A1 | 5/2012 | Carney |
| 2012/0234475 | A1 | 9/2012 | Paldey |
| 2012/0238984 | A1 | 9/2012 | Paldey |
| 2013/0165883 | A1 | 6/2013 | Kimura et al. |
| 2013/0309439 | A1 | 11/2013 | Close et al. |
| 2014/0023822 | A1 | 1/2014 | Tai et al. |
| 2014/0039434 | A1 | 2/2014 | Xu et al. |
| 2014/0052088 | A1 | 2/2014 | Weisman et al. |
| 2014/0054827 | A1 | 2/2014 | Mullane et al. |
| 2014/0121621 | A1 | 5/2014 | Biggs et al. |
| 2014/0121623 | A1 | 5/2014 | Biggs et al. |
| 2014/0121624 | A1 | 5/2014 | Biggs et al. |
| 2014/0121625 | A1 | 5/2014 | Biggs et al. |
| 2014/0121626 | A1 | 5/2014 | Butler et al. |
| 2014/0127459 | A1 * | 5/2014 | Xu .................. A61F 13/51121 428/141 |
| 2014/0163500 | A1 | 6/2014 | Roe et al. |
| 2014/0163501 | A1 | 6/2014 | Ehrnsperger et al. |
| 2014/0170367 | A1 | 6/2014 | Turner et al. |
| 2014/0276517 | A1 | 9/2014 | Chester et al. |
| 2014/0324009 | A1 * | 10/2014 | Lee ..................... A61F 13/512 604/384 |
| 2014/0358101 | A1 * | 12/2014 | Kanya .................. D04H 1/4291 604/366 |
| 2014/0367290 | A1 | 12/2014 | Nomoto et al. |
| 2015/0059599 | A1 | 3/2015 | Boegli |
| 2015/0073366 | A1 | 3/2015 | Ehrnsperger et al. |
| 2015/0173975 | A1 * | 6/2015 | Harumoto ........... A61F 13/5116 604/370 |
| 2015/0182386 | A1 | 7/2015 | Nakakado |
| 2015/0283001 | A1 | 10/2015 | Arizti et al. |
| 2015/0283003 | A1 * | 10/2015 | Rosati ................. A61F 13/5126 206/526 |
| 2016/0040337 | A1 * | 2/2016 | Dutkiewicz ............ D04H 1/559 428/172 |
| 2016/0083880 | A1 | 3/2016 | Hammons et al. |
| 2017/0135872 | A1 * | 5/2017 | Moriya ............. A61F 13/51104 |
| 2018/0001591 | A1 * | 1/2018 | Dutkiewicz ......... A61F 13/537 |
| 2019/0183693 | A1 * | 6/2019 | Suzuki ................ A61F 13/5116 |

FOREIGN PATENT DOCUMENTS

| | | |
|---|---|---|
| EP | 861646 | 5/2003 |
| EP | 1208828 | 7/2005 |

(56) References Cited

FOREIGN PATENT DOCUMENTS

| | | |
|---|---|---|
| EP | 1184075 | 1/2007 |
| EP | 1842513 | 10/2007 |
| EP | 1787611 | 9/2011 |
| EP | 2554730 | 2/2013 |
| EP | 1982013 | 6/2013 |
| EP | 1774940 | 9/2013 |
| EP | 2437708 | 9/2013 |
| EP | 2277485 | 5/2014 |
| JP | 02055058 | 5/1996 |
| JP | 3124190 | 1/2001 |
| JP | 3868880 | 1/2007 |
| JP | 3880502 | 2/2007 |
| JP | 4184253 | 11/2008 |
| JP | 4282428 | 6/2009 |
| JP | 2009153731 A | 7/2009 |
| JP | 2009172354 | 8/2009 |
| JP | 4338327 | 10/2009 |
| JP | 2011200446 | 10/2011 |
| JP | 2012010884 | 1/2012 |
| JP | 4901425 | 3/2012 |
| JP | 4931580 | 5/2012 |
| JP | 4974524 | 7/2012 |
| JP | 5074174 | 11/2012 |
| JP | 5099752 | 12/2012 |
| JP | 5103100 | 12/2012 |
| JP | 5148182 | 2/2013 |
| JP | 2013074978 | 4/2013 |
| JP | 2013126455 | 6/2013 |
| JP | 5268416 | 8/2013 |
| JP | 2013169388 | 9/2013 |
| JP | 5319367 | 10/2013 |
| WO | WO 9301781 | 2/1993 |
| WO | WO 9827904 | 7/1998 |
| WO | WO 200029199 | 5/2000 |
| WO | WO 2000/38604 | 7/2000 |
| WO | WO 200174281 | 10/2001 |
| WO | WO 200224133 | 3/2002 |
| WO | WO 200429349 | 4/2004 |
| WO | WO 2004058214 A1 | 7/2004 |
| WO | WO 2004098869 | 11/2004 |
| WO | WO 2006007149 | 1/2006 |
| WO | WO 2006009997 A2 | 1/2006 |
| WO | WO 2007001270 | 1/2007 |
| WO | WO 2007116944 | 10/2007 |
| WO | WO 2008146594 | 12/2008 |
| WO | WO 2009139255 | 11/2009 |
| WO | WO 201074205 | 7/2010 |
| WO | WO 2010118272 | 10/2010 |
| WO | WO 2011142272 | 11/2011 |
| WO | WO 2012176656 | 12/2012 |
| WO | WO 201347890 | 4/2013 |
| WO | WO 201377074 | 5/2013 |
| WO | WO 2013399463 | 7/2013 |
| WO | WO 2013147222 | 10/2013 |
| WO | WO 2013175360 | 11/2013 |
| WO | WO 2014084066 | 6/2014 |
| WO | WO 201545842 | 4/2015 |
| WO | WO 2016/159952 | 10/2016 |
| WO | WO 2017030136 | 2/2017 |

OTHER PUBLICATIONS

All Office Actions for U.S. Appl. No. 14/844,026.
All Office Actions for U.S. Appl. No. 14/844,033.
All Office Actions for U.S. Appl. No. 14/844,037.
International Search Report and Written Opinion, PCT/US2017/020338, dated May 22, 2017.
All Office Actions for U.S. Appl. No. 14/844,043.
All Office Actions for U.S. Appl. No. 14/844,047.
All Office Actions for U.S. Appl. No. 14/844,292.
All Office Actions for U.S. Appl. No. 14/844,343.
All Office Actions for U.S. Appl. No. 14/844,358.
All Office Actions for U.S. Appl. No. 14/844,374.
All Office Actions for U.S. Appl. No. 14/844,385.
All Office Actions for U.S. Appl. No. 14/844,402.
All Office Actions for U.S. Appl. No. 14/844,411.
All Office Actions for U.S. Appl. No. 14/844,256.
All Office Actions for U.S. Appl. No. 14/844,269.
All Office Actions for U.S. Appl. No. 14/844,459.
All Office Actions for U.S. Appl. No. 14/844,499.
All Office Actions for U.S. Appl. No. 14/844,526.
All Office Actions for U.S. Appl. No. 14/844,457.
All Office Actions for U.S. Appl. No. 14/844,507.
All Office Actions for U.S. Appl. No. 14/844,523.
All Office Actions for U.S. Appl. No. 14/844,543.
All Office Actions for U.S. Appl. No. 14/844,582.
All Office Actions for U.S. Appl. No. 14/844,591.
All Office Actions for U.S. Appl. No. 14/844,603.
All Office Actions for U.S. Appl. No. 14/844,613.

* cited by examiner

ABSORBENT ARTICLE COMPRISING A TOPSHEET/ACQUISITION WEB LAMINATE

CROSS REFERENCE TO RELATED APPLICATION

This application claims priority under 35 U.S.C. § 119 to European Patent Application Serial No. 16159086.4, filed on Mar. 8, 2016, the entire disclosure of which is hereby incorporated by reference.

FIELD OF THE INVENTION

The invention provides an absorbent article for personal hygiene such as a baby diaper, a training pant, a feminine hygiene sanitary napkin or an adult incontinence product. The absorbent article comprises a topsheet/acquisition web laminate.

BACKGROUND OF THE INVENTION

An absorbent article typically comprises a topsheet, a backsheet, and an absorbent core disposed between the topsheet and the backsheet. The absorbent article can further include an acquisition web and optionally a distribution layer. The acquisition web is able to receive the liquid bodily exudates from the topsheet in order to temporary store them. Then, the optional distribution layer can receive the liquid bodily exudates from the acquisition web and distribute and transfer them to the absorbent core. Such absorbent articles exhibit satisfactory fluid handling properties.

Three-dimensional structures have been developed; see for example U.S. Patent Application Publ. No. 2014/0121625 A1.

In order to address consumer acceptance of absorbent articles, a great deal of effort has been spent to increase the opacity of the layers of absorbent articles. Opacity is advantageous in that increased opacity helps disguise waste materials absorbed or contained in or underneath layers of absorbent articles. Thus, it would be desirable to create a nonwoven laminate that has an increased opacity.

Moreover, at the end of the manufacturing process, the absorbent articles are typically folded and packaged as is known in the art. The absorbent articles may be packed under relatively high compression so as to reduce the size of the packages, while still providing an adequate amount of absorbent articles per package. However, the compression applied on the absorbent articles may have negative effects on the three-dimensional structure. Indeed, the three-dimensional structure may be deformed or collapsed which may affect the fluid handling properties of the absorbent article.

Thus, there is a need to provide an absorbent article that presents an improved resiliency to the compression forces.

Finally, there is a need to develop an absorbent article which can provide improved fluid handling properties such as improving the dewatering of the topsheet of the absorbent article.

SUMMARY OF THE INVENTION

An absorbent article for personal hygiene is provided and comprises a longitudinal axis, a transversal axis perpendicular to the longitudinal axis, a topsheet/acquisition web laminate, a liquid impermeable backsheet, and an absorbent core. The absorbent core is located between the topsheet/acquisition web laminate and the backsheet. The topsheet/acquisition web laminate comprises a liquid permeable topsheet and an acquisition web in a face to face relationship. The topsheet/acquisition web laminate comprises three-dimensional protrusions extending from a plane of the topsheet/acquisition web laminate. The acquisition web is a nonwoven fibrous web comprising an upper layer facing towards the topsheet and a lower layer facing towards the absorbent core. The average diameter of the fibers in the upper layer is higher than the average diameter of the fibers in the lower layer.

The lower layer may comprise a mixture of a first type of fibers having a diameter from about 3.5 to about 10 denier and of a second type of fibers having a diameter from about 0.8 to about 2.5 denier.

The second type of fibers may constitute at least 30%, preferably at least 40% of the total weight of the lower layer.

The diameter of the fibers in the upper layer is from about 3.5 to about 10 denier.

The acquisition web may comprise an upper layer with fibers having a diameter from about 3.5 to about 10 denier and a lower layer having a first type of fibers with a diameter from about 3.5 to about 10 denier and a second type of fibers with a diameter from about 0.8 to about 2.5 denier.

The difference of fibers diameter between the upper layer and the lower layer of the acquisition web creates a capillary gradient within the acquisition web. This capillary gradient improves the dewatering of the topsheet of the topsheet/acquisition web laminate. Thus, the topsheet/acquisition web laminate can help to reduce the contact of the liquid bodily exudates with the skin of the wearer. The fluid handling properties of the absorbent article can be improved.

Moreover, the structure of the acquisition web reinforces the structure of the three-dimensional protrusions of the topsheet/acquisition web laminate. Hence, the majority of the three-dimensional protrusions can be better preserved after being subjected to any inherent compressive forces. The topsheet/acquisition web laminate can thereby have an improved resiliency to the compression forces.

Furthermore, having fibers of relatively small diameter within the acquisition web may increase the opacity of the acquisition web of the topsheet/acquisition web laminate. Therefore, the liquid exudates material can be better disguised. The three-dimensional protrusions may also become more visible which brings a perceptional comfort to the user of the absorbent article.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definition of Terms

Figure 1:
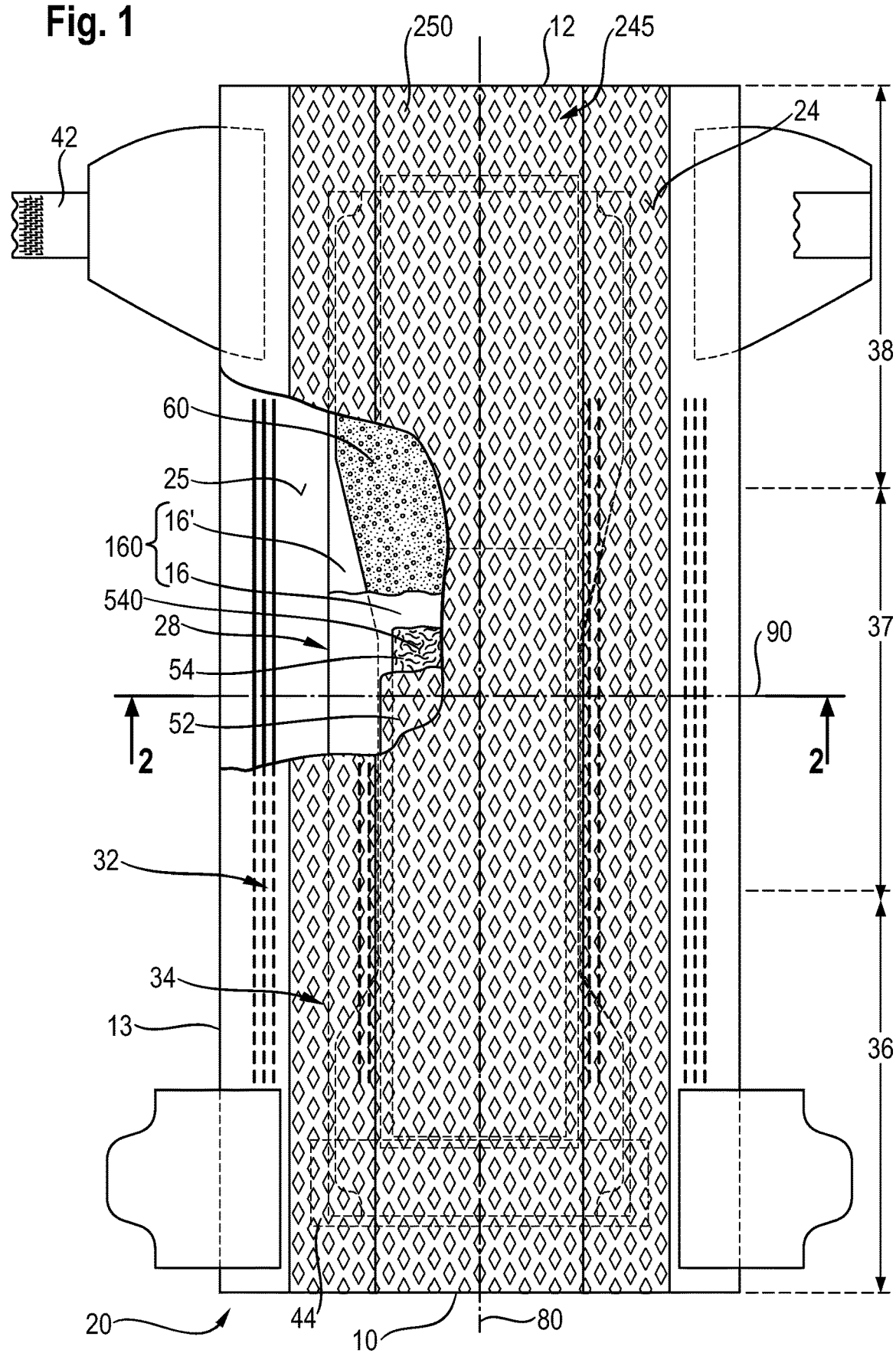
FIG. 1 is an absorbent article in the form of a diaper comprising a topsheet/acquisition web laminate according to the invention with some layers partially removed to show internal structures (or elements)
Figure 2:
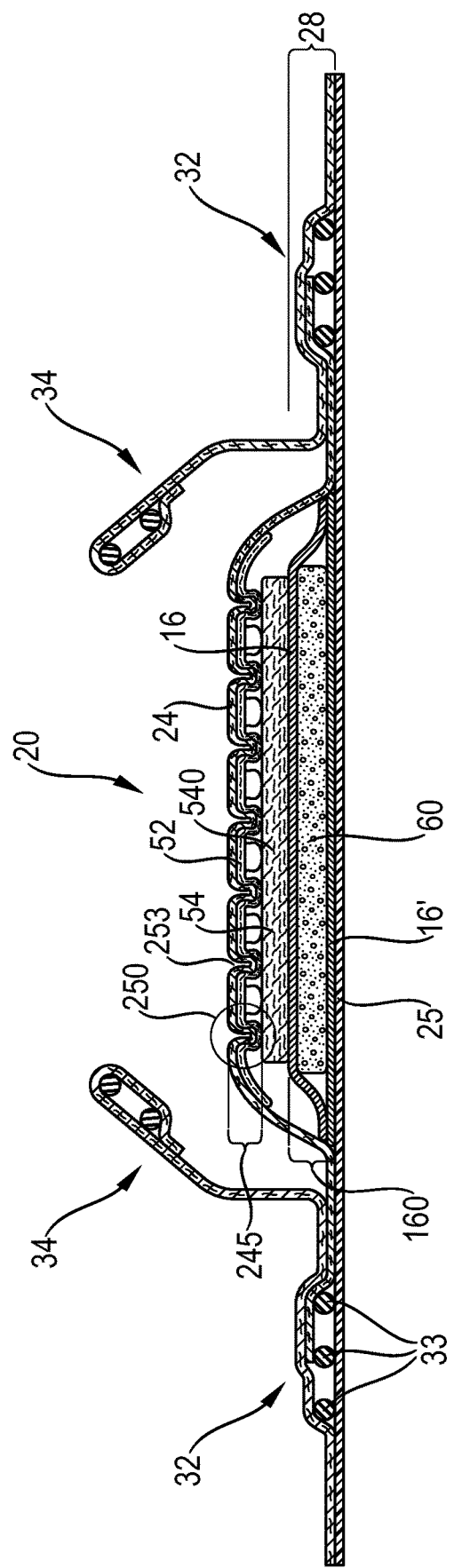
FIG. 2 is a transversal cross-section of the diaper of FIG. 1.

The term "absorbent article" as used herein refers to disposable products such as diapers, pants or feminine hygiene sanitary napkins and the like which are placed against or in proximity to the body of the wearer to absorb and contain the various liquid bodily exudates discharged from the body. Typically these absorbent articles comprise a topsheet, backsheet, an absorbent core, an acquisition web and optionally a distribution layer and other components, with the absorbent core normally placed between the backsheet and the acquisition system or topsheet. The absorbent article of the present invention may be a diaper or pant.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

The term "pant" as used herein refers to an absorbent article having fixed edges, a waist opening and leg openings designed for infant or adult wearers. A pant is placed in position on the wearer by inserting the wearer's legs into the leg openings and sliding the pant-type absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened).

The terms "autogenously bonding", "autogeneously bonded" and "autogenous bond" refer to bonding between discrete fibers of a nonwoven fibrous web using through-air bonding. Autogenous bonding does not apply solid contact pressure such as is applied for point-bonding or calendaring processes and is done independently of externally added additives which promote or facilitate bonding, such as adhesives, solvents, and the like.

The term "bicomponent" refers to fibers having a cross-section comprising two discrete polymer components, two discrete blends of polymer components, or one discrete polymer component and one discrete blend of polymer components. "bicomponent fiber" is encompassed within the term "Multicomponent fiber." A bicomponent fiber may have an overall cross section divided into two subsections of the differing components of any shape or arrangement, including, for example, concentric core/sheath subsections, eccentric core/sheath subsections, side-by-side subsections, radial subsections, etc.

The term "extensible" as used herein refers to a material, which, upon application of a force, is capable of undergoing an apparent elongation of equal to or greater than at least 100% of its original length in the machine and/or cross-machine directions at or before reaching the breaking force if subjected to the following test:

The MD and CD tensile properties are measured using a method using WSP 110.4 (05) Part B, with a 50 mm sample width, 60 mm gauge length, and 60 mm/min rate of extension.

It may be desirable that a material is capable of undergoing an apparent elongation of equal to or greater than at least 100% or 110% or 120% or 130% up to 200% in the machine and/or cross-machine directions at or before reaching the breaking force according to the Test Method as set out above.

If a material is capable of undergoing an apparent elongation of less than 100% of its original length if subjected to the above described test, it is "non-extensible" as used herein.

The term "topsheet/acquisition web laminate" as used herein refers to an intimate combination of a topsheet with an acquisition web, both disposed in a face to face relationship. The topsheet has a first and second surface. The first surface of the topsheet is facing towards the body of the wearer when the absorbent article is in use. The acquisition web has a first surface and a second surface. The second surface of the acquisition web is facing towards the backsheet. The topsheet and the acquisition web can have undergone a simultaneous and joint mechanical deformation while the topsheet and the acquisition web are combined with each other. The topsheet/acquisition web laminate comprises deformations forming three-dimensional protrusions. In the topsheet/acquisition web laminate, the topsheet and acquisition web may be in an intimate contact with each other.

Figures 8A, 8B:
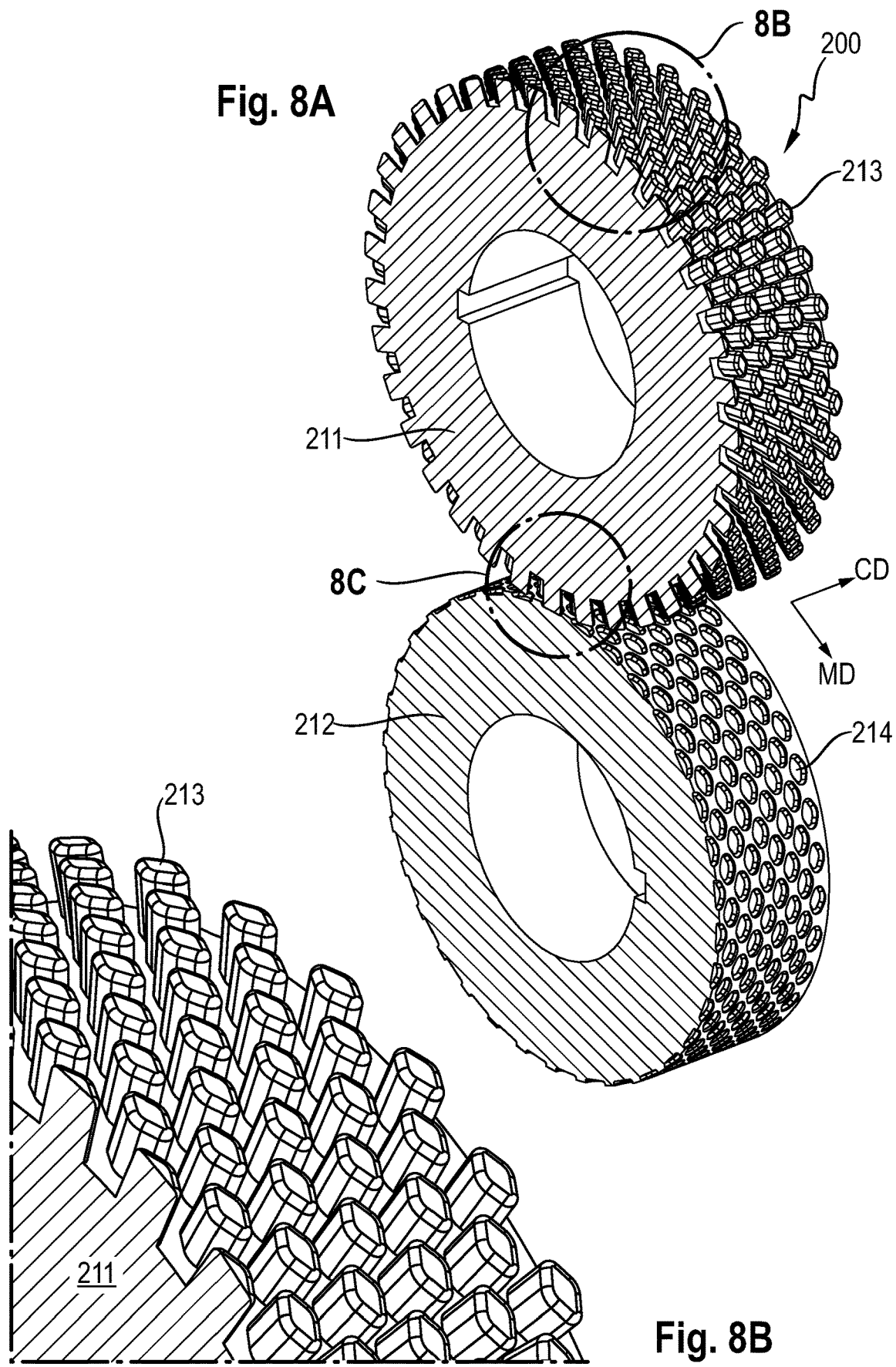
FIG. 8A is a perspective view of an apparatus comprising a first and second forming member for forming the topsheet/acquisition web laminate of the present invention.
FIG. 8B is a perspective view of a portion of the first forming member of the apparatus shown in FIG. 8A.

The topsheet/acquisition web laminate may be formed by nesting together the topsheet and acquisition web, whereby the three-dimensional protrusions of the topsheet coincide with and fit together with the three-dimensional protrusions of the acquisition web, as shown in FIGS. 8A, 8B and 8A. The topsheet/acquisition web laminate comprises deformations forming three-dimensional protrusions.

The term "a majority of the three-dimensional protrusions" as used herein means that more than 50% or more than 60% or more than 70% or more than 80% but not more than 95% of the three-dimensional protrusions of the topsheet/acquisition web laminate.

The term "mechanically deforming and combining" as used herein means that the topsheet and acquisition web are put in a face to face relationship and can be simultaneously mechanically deformed between a first and second roll and intimately combined at the same time. The mechanical deformation of the topsheet and acquisition web depends on the process, the required apparatus but also on the properties of the topsheet and acquisition web, i.e. apparent elongation of the fibers, fiber mobility, ability to deform and stretch in the area where the three-dimensional protrusions of the topsheet/acquisition web laminate are formed, ability to undergo plastic deformation which sets after existing the first and second roll, or springing partially back due to elastic recovery. The mechanical deformation may comprise engaging the topsheet and the acquisition web together between a first and second forming member such that a plurality of deformations comprising three-dimensional protrusions are obtained. The three-dimensional protrusions are formed from the fibers of the topsheet and the acquisition web.

The term "interruptions", as used herein, refers to holes formed in the topsheet and/or acquisition web during the formation of the topsheet/acquisition web laminate, and does not include the pores and interstices between fibers typically present in nonwovens.

The term "cellulosic fiber" as used herein refers to natural fibers which typically are wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web.

The term "dry-laid fiber" as used herein means fibers which have been provided in a fluid medium which is gaseous (air).

The term "wet-laid fiber" as used herein comprises cellulosic fibers which have been suspended in an aqueous medium, such as water, before being converted into a web and dried according to a wet-laid papermaking process.

The term "web" as used herein means a material capable of being wound into a roll. Webs may be nonwovens.

The term "nonwoven web" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

Any preferred or exemplary embodiments described below are not limiting the scope of the claims, unless specifically indicated to do so. The words "typically", "normally", "advantageously" and the likes also qualify features which are not intended to limit the scope of the claims unless specifically indicated to do so.

General Description of the Absorbent Article 20

Figure 3:
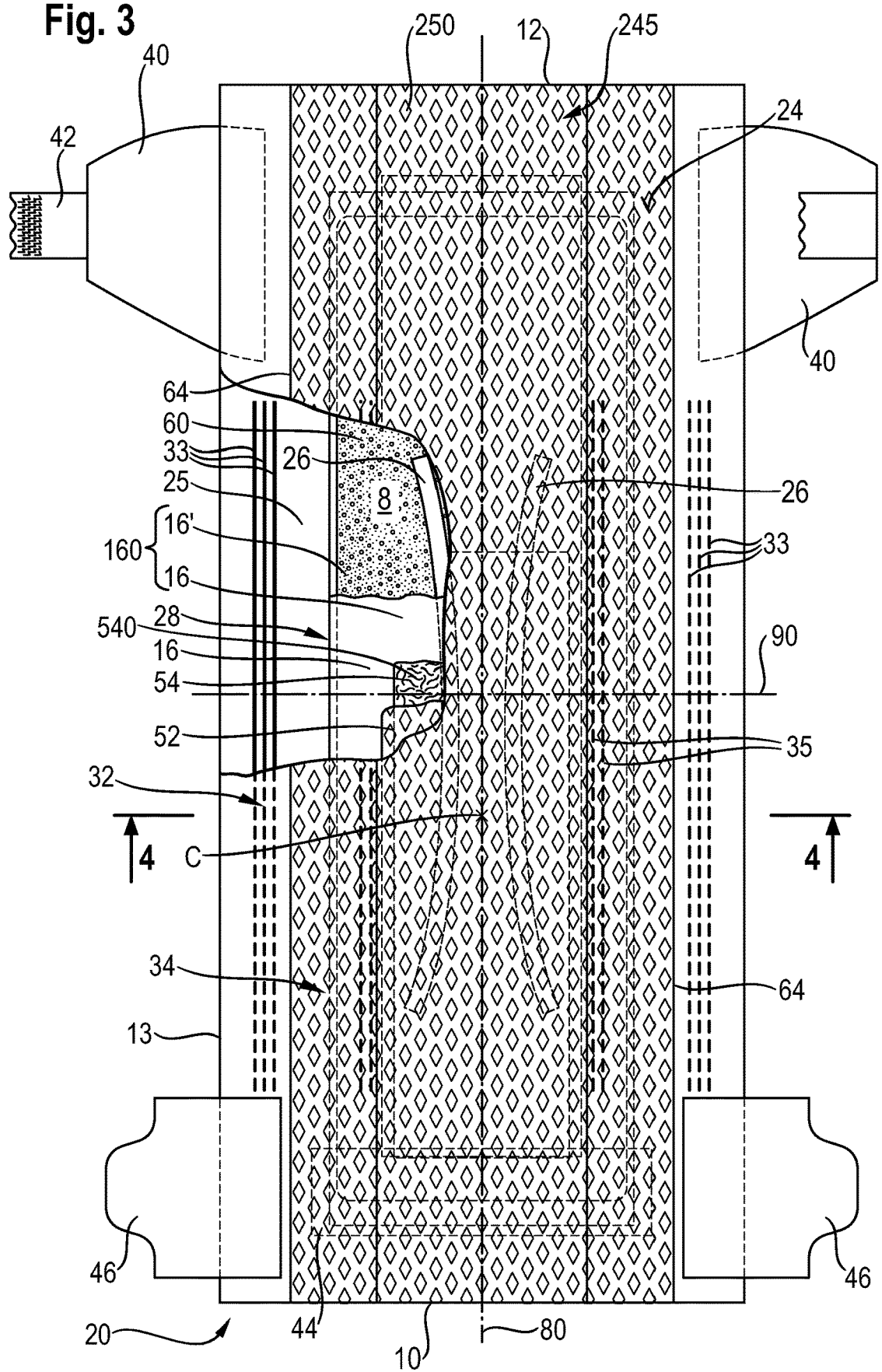
FIG. 3 is an absorbent article in the form of a diaper comprising a topsheet/acquisition web laminate according to the present invention with another type of absorbent core with some layers partially removed to show internal structures (or elements)

An exemplary absorbent article 20 in which the absorbent core 28 of the invention can be used is a taped diaper 20 as represented in FIG. 1 and FIG. 3 with a different absorbent core construction. FIG. 1 and FIG. 3 are top plan views of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles.

The absorbent article 20 comprises a topsheet/acquisition web laminate 245 formed from a liquid permeable topsheet 24 and an acquisition web 52. In other words, the absorbent article 20 comprises a liquid permeable topsheet 24 and an acquisition web 52 wherein the topsheet 24 and acquisition web 52 are joined to form a topsheet/acquisition web laminate 245.

The absorbent article 20 comprises a liquid impermeable backsheet 25 and an absorbent core 28 between the topsheet 24 and the backsheet 25. The absorbent article 20 comprises a front edge 10, a back edge 12, and two longitudinal side edges 13. The front edge 10 is the edge of the absorbent article 20 which is intended to be placed towards the front of the user when worn, and the back edge 12 is the opposite edge.

The absorbent article 20 may be notionally divided by a longitudinal axis 80 extending from the front edge 10 to the back edge 12 of the absorbent article 20 and dividing the absorbent article 20 in two substantially symmetrical halves relative to this axis, when viewing the absorbent article 20 from the wearer facing side in a flat out configuration, as exemplarily shown in FIG. 1 and FIG. 3.

The absorbent article 20 may comprise a distribution layer 54 which may comprise a dry-laid fibrous structure or a wet-laid fibrous structure located between the topsheet/acquisition web laminate 245 and the absorbent core 28. The topsheet/acquisition web laminate 245 is facing towards the body of the wearer when the absorbent article is in use.

The distribution layer 54 may comprise a dry-laid fibrous structure. The dry-laid fibrous structure may comprise dry-laid fibers 540. The dry-laid fibrous structure may comprise a mixture including dry-laid fibers and superabsorbent polymers. The dry-laid fibers may comprise intra-fiber cross-linked cellulosic fibers.

The distribution layer 54 may comprise a wet-laid fibrous structure. The wet-laid fibrous structure may comprise wet-laid fibers.

The distribution layer may typically have an average basis weight of from 30 to 400 g/m2, in particular from 100 to 300 g/m2. The density of the distribution layer may vary depending on the compression of the article, but may be of between 0.03 to 0.15 g/cm3, in particular 0.08 to 0.10 g/cm3 measured at 0.30 psi (2.07 kPa).

The distribution layer 54 may be free of tow fibers.

The distribution layer 54 may for example comprise at least 50% by weight of cross-linked cellulose fibers. The cross-linked cellulosic fibers may be crimped, twisted, or curled, or a combination thereof including crimped, twisted, and curled. Exemplary chemically cross-linked cellulosic fibers suitable for a distribution layer 54 are disclosed in U.S. Pat. Nos. 5,549,791; 5,137,537; WO95/34329 or U.S. Pat. Appl. Publ. No. 2007/118087. Exemplary cross-linking agents may include polycarboxylic acids such as citric acid and/or polyacrylic acids such as acrylic acid and maleic acid copolymers.

A carrier layer may be disposed between the topsheet/acquisition web laminate 245 and the distribution layer 54. According to the method used for making the three-dimensional structure of the topsheet/acquisition web laminate 245, when the topsheet 24 and acquisition web 52 are mechanically deformed together, holes might unintentionally occur. When the distribution layer 54 comprises a dry-laid fibrous structure, the fibers 540 of the dry-laid fibrous structure may pass through the unintentional holes formed at the topsheet/acquisition web laminate 245 and contact undesirably the skin of the wearer. The carrier layer may act as a barrier layer to impede the fibers 540 of dry-laid fibrous structure from passing through the holes of the topsheet/acquisition web laminate 245 unintentionally formed by the three-dimensional mechanical deformation of the topsheet 24 with the acquisition web 52. Also, the carrier layer may help the transfer of the liquid bodily exudates from the topsheet/acquisition web laminate 245 to the dry-laid fibrous structure.

Alternatively, the carrier layer may be disposed between the distribution layer 54 and the absorbent core 28. Hence, the carrier layer may help to distribute and transfer of the liquid bodily exudates from the distribution layer 54 to the absorbent core 28 which enables more efficient use of the absorbent core 28.

The carrier layer may be selected from the group consisting of nonwovens, or films and combinations thereof. Examples of a nonwoven web used for the carrier layer may include various types of known nonwoven webs such as a spunbonded nonwoven web, a meltblown nonwoven web, a spunbond-meltblown-spunbond nonwoven web. These nonwoven webs are made of thermoplastic polymers.

A material for fibers composing the nonwoven web used for the carrier layer may include various types of known fibers such as polyethylene, polypropylene, polyester, and acryl, conjugate fibers such as polyethylene/polypropylene, polyethylene/polyethylene terephthalate, and polypropylene/polyethylene terephthalate, i.e., fibers formed of core-in-sheath fibers and side-by-side fibers. The fibers may be used alone or in combination. Further, the carrier layer may have a monolayer structure or a multilayer structure.

The carrier layer may have a basis weight of at least 5 gsm to 60 gsm or at least 5 gsm to 20 gsm or at least 5 to 15 gsm.

As explained in more detail below, the topsheet/acquisition web laminate 245 comprises the topsheet 24 and the acquisition web 52 in a face to face relationship. The topsheet/acquisition web laminate 245 comprises three-dimensional protrusions 250. For this, the topsheet 24 and the acquisition web 52 can be simultaneously mechanically deformed and combined together in a face to face relationship such that a topsheet/acquisition web laminate 245 is formed. The topsheet/acquisition web laminate 245 comprises mechanical deformations forming three-dimensional protrusions 250 extending from a plane of the topsheet/acquisition web laminate 245. The mechanical deformations provide a three-dimensional structure to the topsheet/acquisition web laminate 245.

Figure 5:
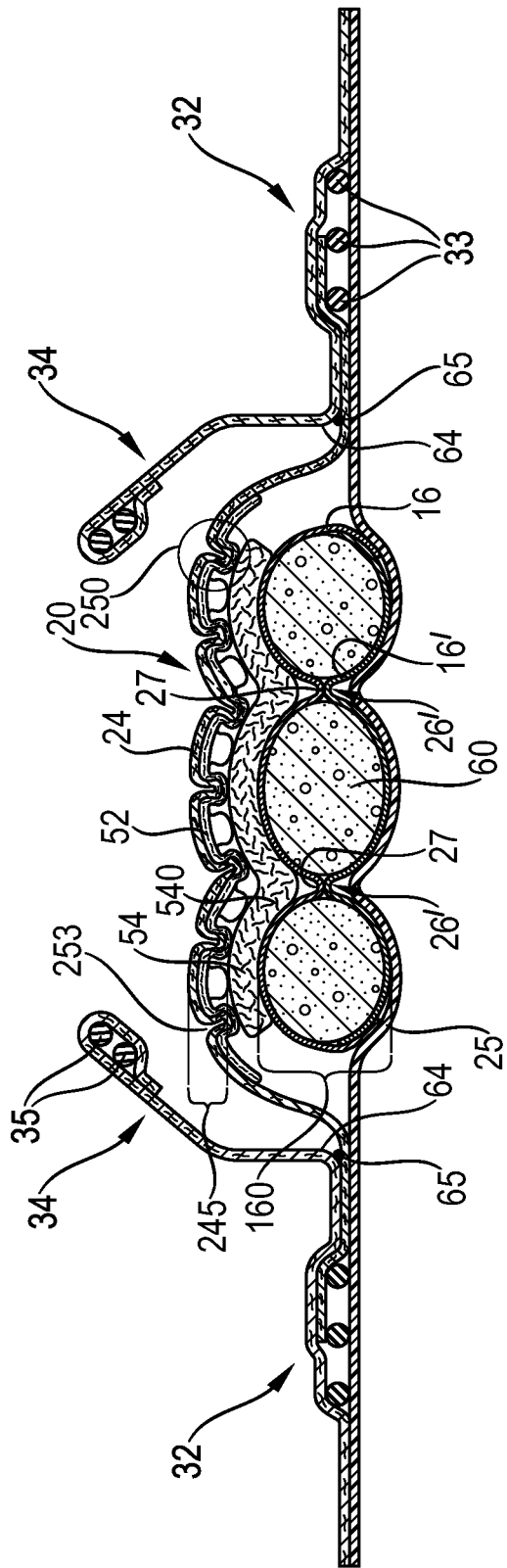
FIG. 5 is a transversal cross-section of the absorbent article of FIG. 3 taken at the same point as FIG. 4 when the absorbent article is loaded with liquid bodily exudates.

The absorbent article 20 may comprise elasticized gasketing cuffs 32 present between the topsheet 24 and the backsheet 25 and upstanding barrier leg cuffs 34. As shown in FIG. 5, the barrier leg cuffs 34 may be delimited by a proximal edge 64 joined to the rest of the article, typically the topsheet and/or the backsheet, and a free terminal edge intended to contact and form a seal with the wearer's skin. The barrier leg cuffs 34 may be joined at the proximal edge 64 by a bond 65 which may be made for example by adhesive bonding, fusion bonding or combination of known bonding means. Each barrier leg cuff 34 may comprise one, two or more elastic strings 35 to provide a better seal. The gasketing cuffs 32 may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 for example between the topsheet and backsheet in the area of the leg openings.

FIGS. 1 and 3 also show other typical diaper components such as a fastening system comprising fastening tabs 42 attached towards the back edge 12 of the absorbent article 20 and cooperating with a landing zone 44 towards the front edge 10 of the absorbent article 20. The absorbent article 20 may also comprise front ears 46 and back ears 40 as it is known in the art.

The absorbent article 20 may also comprise other typical components, which are not represented in the Figures, such as a back elastic waist feature, a front elastic waist feature, transverse barrier cuff(s), a lotion application, etc.

The absorbent article 20 can also be notionally divided by a transversal axis 90 in a front region and a back region of equal length measured on the longitudinal axis, when the absorbent article 20 is in a flat state. The absorbent article's transversal axis 90 is perpendicular to the longitudinal axis 80 and placed at half the length of the absorbent article 20. The length of the absorbent article 20 can be measured along the longitudinal axis 80 from the front edge 10 to the back edge 12 of the absorbent article 20. The topsheet 24, acquisition web 52, distribution layer 54 and absorbent core 28 each have a width which can be measured from their respective longitudinal edges and in parallel to the transversal axis 90.

The absorbent article 20 is notionally divided in a front region 36, a back region 38 and a crotch region 37 located between the front and the back region of the absorbent article 20. Each of the front, back and crotch region is ⅓ of the length of the absorbent article 20 in a direction parallel to the longitudinal axis.

The acquisition web 52 in the topsheet/acquisition web laminate 245 may be positioned in the front region 36, in the crotch region 37 and in the back region 38.

The acquisition web 52 in the topsheet/acquisition web laminate 245 may be positioned only in the front region 36 and in the crotch region 37 of the absorbent article 20. Such arrangement can help to acquire and distribute the liquid bodily exudates such as urine, around the pee point where liquid is initially introduced into the absorbent article.

The acquisition web 52 in the topsheet/acquisition web laminate 245 may be positioned only in the back region 38 and in the crotch region 37 of the absorbent article 20. Such arrangement can help to acquire the feces of the wearer, especially when the feces have a low viscosity.

The absorbent core 28 of the present invention may comprise as absorbent material 60 a blend of cellulosic fibers (so called "airfelt") and superabsorbent polymers (SAP) in particulate form encapsulated in one or more substrates, see for example U.S. Pat. No. 5,151,092 (Buell). Alternatively, the absorbent core 28 may be airfelt free as described in detail below.

The absorbent core 28 of the present invention may comprise as absorbent material 60 a blend of cellulosic fibers (so called "airfelt") and superabsorbent polymers in particulate form encapsulated in one or more substrates, see for example U.S. Pat. No. 5,151,092 (Buell). Alternatively, the absorbent core 28 may be airfelt free as described in detail below.

The term "absorbent core" does not include an acquisition web or distribution layer or any other component of an absorbent article which is not either an integral part of the core wrap or placed within the core wrap. The absorbent core is typically the component of an absorbent article which has the highest absorbent capacity of all the components of the absorbent article.

Generally, the absorbent core 28 can be defined by the periphery of the layer formed by the absorbent material 60 within the core wrap 160, as seen from the top side of the absorbent core 28. The absorbent core 28 can take various shapes, in particular display a so-called "dog bone" or "hour-glass" shape, which shows a tapering along its width towards the middle or "crotch" region of the core. In this way, the absorbent core 28 may have a relatively narrow width in an area of the absorbent core 28 intended to be placed in the crotch region of the absorbent article. This may provide for example better wearing comfort. The absorbent core 28 may thus have a width (as measured in the transversal direction) at its narrowest point which is less than about 100 mm, 90 mm, 80 mm, 70 mm, 60 mm or even less than about 50 mm. The absorbent core 28 can also be generally rectangular, see for example as shown in FIG. 1, but other deposition areas can also be used such as a "T" or "Y" or "hour-glass" or "dog-bone" shape.

Some components of the absorbent article 20 will now be discussed in more details.

"Airfelt-free" Absorbent Core 28

The absorbent core 28 of the absorbent article 20 may comprise an absorbent material 60 enclosed within a core wrap 160. The absorbent material 60 may comprise from 80% to 100% of SAP, such as SAP particles, by total weight of the absorbent material 60. The core wrap 160 is not considered as an absorbent material 60 for the purpose of assessing the percentage of SAP in the absorbent core 28.

The term "superabsorbent polymers" (herein abbreviated as "SAP") as used herein refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 25 g/g, or from 20 to 50 g/g, or from 20 to 40 g/g, or 25 to 35 g/g.

By "absorbent material" it is meant a material which has at least some absorbency and/or liquid retaining properties, such as SAP, cellulosic fibers as well as some hydrophilically treated synthetic fibers. Typically, adhesives used in making absorbent cores have no absorbency properties and are not considered as absorbent material. The SAP content may be substantially higher than 80%, for example at least 85%, at least 90%, at least 95% and even up to and including 100% of the weight of the absorbent material 60 contained within the core wrap 160. This above SAP content substantially higher than 80% SAP may provide a relatively thin absorbent core 28 compared to conventional absorbent cores typically comprising between 40-60% SAP and 40-60% of cellulosic fibers. The absorbent material 60 of the invention may in particular comprise less than 10% weight percent, or less than 5% weight percent, or even be substantially free of natural and/or synthetic fibers. The absorbent material 60 may advantageously comprise little or no cellulosic fibers, in particular the absorbent core 28 may comprise less than 15%, 10%, or 5% (airfelt) cellulosic fibers by weight of the absorbent core 28, or even be substantially free of cellulose fibers. Such absorbent core 28 may be relatively thin and thinner than conventional airfelt cores. FIG. 1, FIG. 2, FIG. 3 and FIG. 4 are illustrations of an absorbent article 20 comprising an "airfelt-free" absorbent core 28.

The absorbent material 60 may comprise at least 80% of superabsorbent polymers or at least 95% of superabsorbent polymers, by total weight of the absorbent material.

"Airfelt-free" absorbent cores 28 comprising relatively high amount of SAP with various absorbent core designs have been proposed in the past, see for example in U.S. Pat. No. 5,599,335 (Goldman), EP1447066A1 (Busam), WO95/11652 (Tanzer), US2008/0312622A1 (Hundorf), and WO2012/052172 (Van Malderen).

The absorbent core 28 of the invention may comprise adhesive for example to help immobilizing the SAP within the core wrap 160 and/or to ensure integrity of the core wrap, 160 in particular when the core wrap 160 is made of one or more substrates. The core wrap 160 will typically extend over a larger area than strictly needed for containing the absorbent material 60 within.

Core Wrap 160

The absorbent material 60 is encapsulated in one or more substrates. The core wrap 160 comprises a top side 16 facing the laminate 245 and a bottom side 16' facing the backsheet 25. The core wrap 160 may be made of a single substrate folded around the absorbent material 60. The core wrap 160 may be made of two substrates (one mainly providing the top side 16 and the other mainly providing the bottom side 16') which are attached to another, as exemplarily shown in FIG. 2. Typical configurations are the so-called C-wrap and/or sandwich wrap. In a C-wrap, as exemplarily shown in FIG. 4, the longitudinal and/or transversal edges of one of the substrate are folded over the other substrate to form flaps. These flaps are then bonded to the external surface of the other substrate, typically by bonding with an adhesive. The so called C-wrap construction can provide benefits such as improved resistance to bursting in a wet loaded state compared to a sandwich seal.

The core wrap 160 may be formed by any materials suitable for receiving and containing the absorbent material 60. The core wrap 160 may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, U.S. Pat. Appl. Pub. No. 2011/0268932A1, U.S. Pat. Appl. Pub. No. 2011/0319848A1 or U.S. Pat. Appl. Pub. No. 2011/0250413A1. Nonwoven materials provided from synthetic fibers may be used, such as polyethylene (PE), polyethylene terephthalate (PET) and in particular polypropylene (PP).

"Airfelt-free" Absorbent Core 28 Comprising Substantially Absorbent Material Free Areas 26

The term "substantially free of absorbent material" or "substantially absorbent material free" as used herein means that the basis weight of the absorbent material in the substantially absorbent material free areas is at least less than 10%, in particular less than 5%, or less than 2%, of the basis weight of the absorbent material in the rest of the absorbent core.

As shown in FIG. 3, the absorbent core 28 may comprise an absorbent material deposition area 8 defined by the periphery of the layer formed by the absorbent material 60 within the core wrap 160.

Figure 4:
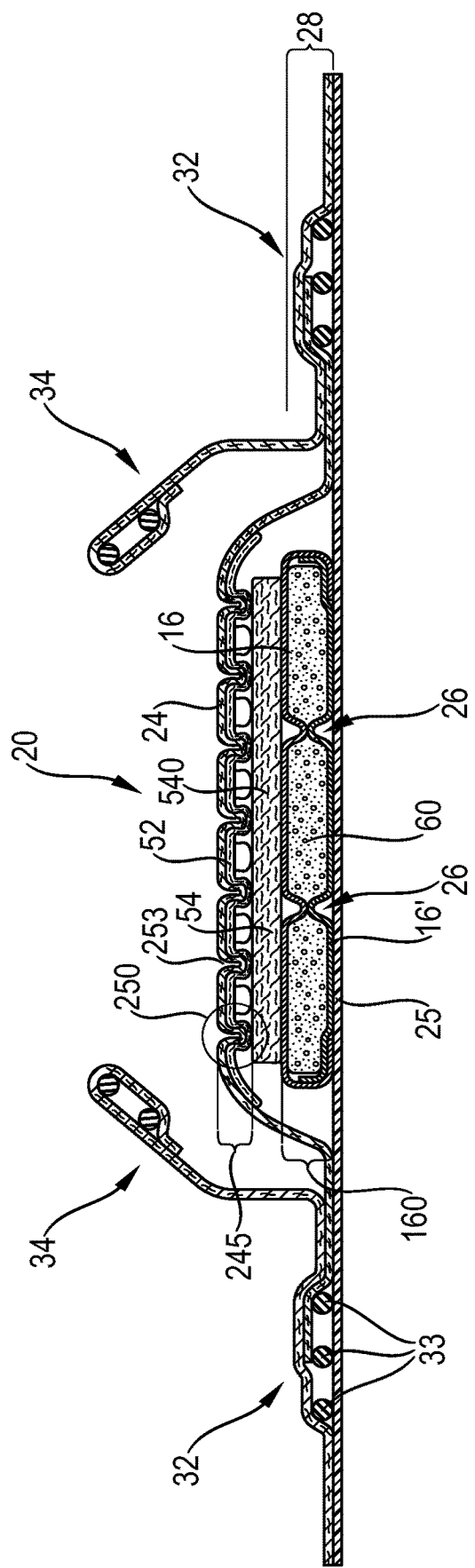
FIG. 4 is a transversal cross-section of a diaper of FIG. 3.

The absorbent core 28 may comprise one or more substantially absorbent material free area(s) 26 which is/are substantially free of absorbent material 60 and through which a portion of the top side 16 of the core wrap 160 is attached by one or more core wrap bond(s) 27 to a portion of the bottom side 16' of the core wrap 160, as shown in FIGS. 3, 4 and 5. In particular, there can be no absorbent material 60 in these areas. Minimal amount such as contaminations with absorbent material 60 that may occur during the making process are not considered as absorbent material 60. The one or more substantially absorbent material free area(s) 26 is/are advantageously confined by the absorbent material 60, which means that the substantially absorbent material free area(s) 26 do(es) not extend to any of the edge of the absorbent material deposition area 8.

If the substantially absorbent material free area 26 extends to any of the edges of the absorbent material deposition area 8, each substantially absorbent material free area 26 may have areas of absorbent material 60 on either side of each substantially absorbent material free area 26.

The absorbent core 28 may comprise at least two substantially absorbent material free areas 26 symmetrically disposed on both sides of the longitudinal axis of the absorbent core 28, as shown in FIG. 3.

The substantially absorbent material free area(s) 26 may be straight and completely oriented longitudinally and parallel to the longitudinal axis but also may be curved or have one or more curved portions.

Furthermore, in order to reduce the risk of liquid bodily exudates leakages, the substantially absorbent material free area(s) 26 advantageously do not extend up to any of the edges of the absorbent material deposition area 8, and are therefore surrounded by and fully encompassed within the absorbent material deposition area 8 of the absorbent core 28. Typically, the smallest distance between a substantially absorbent material free area 26 and the closest edge of the absorbent material deposition area 8 is at least 5 mm.

"Airfelt free" absorbent cores 28 comprising substantially absorbent material free areas 26 have been proposed, see for example in EP Patent Application No. 12196341.7.

As shown in FIG. 5, one or more channel(s) 26' along the substantially absorbent material free area(s) 26 in the absorbent core 28 may start forming when the absorbent material 60 absorbs a liquid and starts swelling. As the absorbent core 28 absorbs more liquid, the depressions within the absorbent core 28 formed by the channel(s) 26' will become deeper and more apparent to the eye and the touch. The formation of the channel(s) 26' may also serve to indicate that the absorbent article 20 has been loaded with liquid bodily exudates. The core wrap bond(s) 27 should remain substantially intact at least during a first phase as the absorbent material 60 absorbs a moderate quantity of liquid bodily exudates.

As shown in FIG. 5, when the absorbent material swells, the core wrap bonds 27 remain at least initially attached in the substantially absorbent material free areas 26. The absorbent material 60 swells in the rest of the absorbent core 28 when it absorbs a liquid, so that the core wrap thus forms channels 26' along the substantially absorbent material free areas 26 comprising the core wrap bonds 27.

Topsheet Materials

The topsheet/acquisition web laminate 245 of the present invention can be made of any suitable nonwoven materials ("precursor materials"). In some cases, the topsheet/acquisition web laminate 245 may also be free of cellulose materials. The precursor materials for the topsheet/acquisition web laminate 245 may have suitable properties in order to be deformed. The suitable properties of the precursor materials may include: apparent elongation of the fibers, fiber mobility, ability to deform and stretch in the area where the three-dimensional protrusions 250 of the topsheet/acquisition web laminate 245 are formed. Hence, the precursor materials are capable of undergoing mechanical deformation to ensure that the three-dimensional protrusion 250 will not tend to recover or return to the prior configuration of a flat topsheet 24 laminated or a flat acquisition web 52.

Several examples of nonwoven materials suitable for use as a topsheet 24 for the topsheet/acquisition web laminate 245 may include, but are not limited to: spunbonded nonwovens; carded nonwovens; and nonwovens with relatively specific properties to be able to be readily deformed.

One suitable nonwoven material as a topsheet 24 for the topsheet/acquisition web laminate 245 may be an extensible polypropylene/polyethylene spunbonded nonwoven. One suitable nonwoven material as a topsheet 24 for the topsheet/ acquisition web laminate 245 may be a spunbonded nonwoven comprising polypropylene and polyethylene. The fibers may comprise a blend of polypropylene and polyethylene. Alternatively, the fibers may comprise bi-component fibers, such as a core/sheath fiber with polyethylene on the sheath and polypropylene in the core of the fiber.

The topsheet 24 of the topsheet/acquisition web laminate 245 may have a basis weight from 8 to 40 gsm or from 8 to 30 gsm or from 8 to 20 gsm.

Acquisition Web Materials

The acquisition web is a nonwoven fibrous web.

Several examples of nonwoven materials suitable for use as the acquisition web 52 for the topsheet/acquisition web laminate 245 may include, but are not limited to: spunbonded nonwovens; carded nonwovens; and nonwovens with relatively specific properties to be able to be readily deformed.

Preferably, the acquisition web is a carded nonwoven fibrous web.

The acquisition web may comprise essentially staple fibers. The acquisition web may, in addition to the staple fibers, comprise of minor amounts of additives, such as odor control additives, perfumes, colored pigments or the like.

The acquisition web 52 may include synthetic fibers made of polypropylene, polyethylene, polyester, polyethylene terephthalate, polybutylene terephthalate, polyamide, and combinations thereof.

Preferably, for the present invention, staple fibers are laid down by a carding process to form a layer of non-consolidated fibers. The layer then undergoes a through-air bonding process to form an autogenously bonded web.

The fibers of the acquisition web 52 are autogenously bonded.

The basis weight of the acquisition web may be from 20 to 100 $g/m^2$, or from 30 to 80 $g/m^2$, or from 40 to 70 $g/m^2$.

Carding Process

Carding is a mechanical process using staple fibers. To obtain staple fibers, the fibers are first spun, cut to a few centimeters length, and put into bales (bundles of compressed fibers). The carding process starts with the opening of the bales of fibres which may be blended and are conveyed to the next stage by air transport. They are then combed into a web by a carding machine, such as a rotating drum or series of drums covered in fine wires or teeth. The precise configuration of cards will depend on the fabric weight and fibre orientation required. The web can be parallel-laid, where most of the fibres are laid in the direction of the web travel, or they can be random-laid. Typical parallel-laid carded webs result in good tensile strength, low elongation and low tear strength in the machine direction and the reverse in the cross direction.

In contrast to carded nonwoven webs, spunlaid and meltblown nonwoven webs are typically made in one continuous process. Fibers are spun and then directly dispersed into a web by deflectors or directed with air streams. The fibers of a spunlaid or meltblown nonwoven are considerably longer compared to staple fibers.

Through Air Bonding

As used herein, through-air bonding or "TAB" means a process of bonding staple fibers of the layer of non-consolidated fibers in which air is forced through the web, wherein the air is sufficiently hot to melt the polymer of a staple fiber or, if the staple fibers are multicomponent fibers, wherein the air is sufficiently hot to melt one of the polymers of which the fibers of the web are made. The air velocity is typically between 30 and 90 meter per minute and the dwell time may be as long as 6 seconds. The melting and resolidification of the polymer provides the bonding between different staple fibers.

Figure 6:
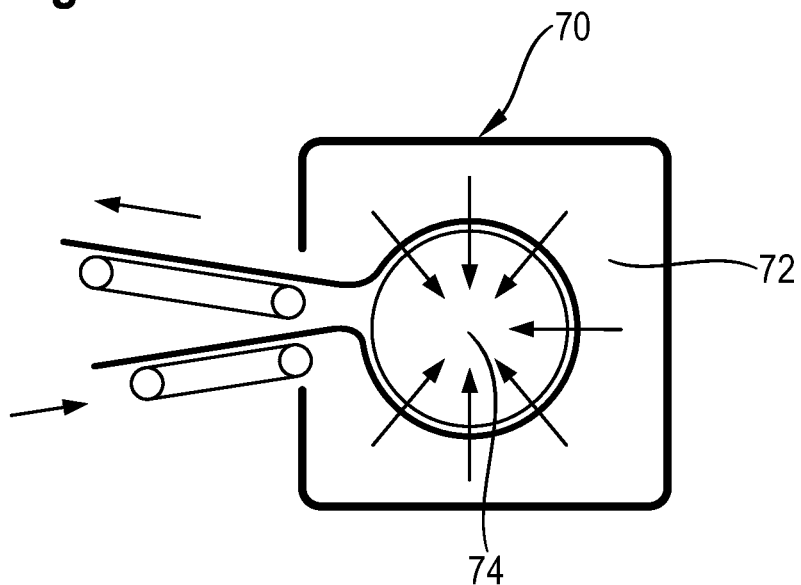
FIG. 6 shows an equipment assembly used in the through air bonding process.

As shown in FIG. 6, in the through-air bonder 70, air having a temperature above the melting temperature of the polymer of the staple fiber or, if the staple fibers are multicomponent fibers, of a first fiber component and below the melting temperature of a second fiber component is directed from the hood 72, through the web, and into the perforated roller 74. Alternatively, the through-air bonder 70 may be a flat arrangement wherein the air is directed vertically downward onto the web. The operating conditions of the two configurations are similar, the primary difference being the geometry of the web during bonding. The hot air melts the staple fiber, or, for multicomponent fibers, the lower melting polymer component and thereby forms bonds between the staple fibers to consolidate and integrate the layer of staple fibers into a web. As an example for a bicomponent fiber, when polypropylene and polyethylene are used as polymer components A and B respectively, the air flowing through the through-air bonder usually has a temperature ranging from about 110° C. to about 162° C. at a velocity from about 30 to about 90 meters per minute. It should be understood, however, that the parameters of the through-air bonder depend on factors such as the type of polymers used and thickness of the fibrous layer.

Spunbonded Process

Spunbonded nonwoven webs are made by melting polymer granules and extruding the molten polymer through spinnerets. The continuous fibers are drawn, cooled and deposited on to a conveyor to form a fibrous layer. The fibrous layer can be consolidated by bonding processes, where the fibrous layer is passed through a pair of calanders. Typically, one calander (the anvil calander) has a smooth surface, whereas the other calander has protrusions extending from its surface to provide a point bonded nonwoven web. Bonding can be achieved by pressure (between the rollers), by heat (e.g. by heating one or both rollers) or by a combination of heat and pressure. Alternatively, consolidation of the fibers to form an integral web can also be done by air through bonding the fibers, by hydroentanglement, by needle punching or by other methods known in the art.

In meltblown web formation, low viscosity polymers are extruded into a high velocity airstream on leaving the spinneret. The extruded fibers are rapidly drawn to fine diameters, solidify and may break into shorter fibers during this drawing and lay down process before collecting the fibers in the form of a fibrous layer. The fibrous layer can be consolidated by the same methods as described above for spunbonded nonwoven webs.

Also, nonwoven webs composed of one or more layers of spunbond fibers and one or more layers of meltblown fibers are well known in the art and generally suitable as acquisition web of the present invention. Examples are SMS (two outer layers of spunbond fibers with one layer of meltblown fibers in between), SMMS, and the like.

Structure of the Acquisition Web 52

The acquisition web 52 is a nonwoven fibrous web comprising an upper layer facing towards the topsheet 24 and a lower layer facing towards the absorbent core 28.

The acquisition web 52 may comprise a first surface and a second surface. The upper layer may form the first surface of the acquisition web 52. The lower layer may form the second surface of the acquisition web 52.

The topsheet 24 may comprise a first surface and a second surface.

The first surface of the acquisition web 52 is in contact with the second surface of the topsheet. In other words, the upper layer is in contact with the second surface of the topsheet 24.

The second surface of the acquisition web 52 is in contact with the underlying layers of the absorbent article 20. In other words, the lower layer of the acquisition web 52 is in contact with the underlying layers of the absorbent article 20.

The upper layer and the lower layer of the acquisition web 52 may include synthetic fibers made of polypropylene, polyethylene, polyester, polyethylene terephthalate, polybutylene terephthalate, polyamide, and combinations thereof.

Preferably, the fibers of the upper layer and of the lower layer of the acquisition web 52 are staple fibers.

The fibers of the acquisition web 52 may be monocomponent fibers or multicomponent fibers.

The monocomponent or multicomponent fibers may be made of polymeric materials, such as polyolefins (e.g. polypropylene, or polyethylene), polyester, polyethylene terephthalate (PET), polybutylene terephthalate, polyamide, and combinations thereof. The polymers may also comprise copolymers such as Co-PET.

Suitable multicomponent fibers may be bicomponent fibers, such as core/sheath bicomponent fibers and side-by-side bicomponent fibers. The core/sheath bicomponent fibers may be concentric or eccentric fibers.

If the fibers of the acquisition web 52 may comprise core/sheath bicomponent fibers, it is desirable that the sheath is made of a polymer which has a melting point below the melting point of the polymer which forms the sheath. If such bicomponent fibers are subjected to through-air bonding, the temperature of the through air bonding process is selected such that the polymer of the sheath is at least partially transferred to a molten state (or to a state where the fiber surface becomes sufficiently tacky) such that the fibers bond together while the core of the bicomponent fiber remains substantially unaffected.

If side-by-side bicomponent fibers may be used, the polymers forming the first and second component may also have different melting points. If such bicomponent fibers are subjected to through-air bonding, the temperature of the through air bonding process is selected such that the polymer of the component having the lower melting point is molten is at least partially transferred to a molten state (or to a state where the fiber surface becomes sufficiently tacky) such that the fibers bond together while the polymer of the component having the higher melting point remains substantially unaffected.

The fibers of the acquisition web 52 may be solid fibers, i.e. fibers which are not hollow.

The shape of the fibers of the acquisition web 52 may be round (i.e. fibers having a circular cross-section). Alternatively, the fibers may have non-round shape, such as multilobal fibers (e.g. trilobal fibers), or flat fibers ("ribbon-like" cross-section). In multilobal fibers, a central section is encircled by a multiplicity of lobes. E.g. in a trilobal fiber, a central section is encircled by three lobes.

The fibers may comprise or consist of a mixture of solid, round bicomponent fibers (such as core/sheath or side-by-side bicomponent fibers) and solid, multilobal (such as trilobal) monocomponent fibers. Alternatively, the fibers may comprise or consist of a mixture of solid, round bicomponent fibers (such as core/sheath or side-by-side bicomponent fibers) and solid, round monocomponent fibers.

The Upper Layer of the Acquisition Web 52

The upper layer of the acquisition web 52 may comprise multicomponent fibers such as core/sheath bicomponent fibers or side-by-side bicomponent fibers. Preferably, the fibers of the upper layer are core/sheath bicomponent fibers.

Preferably, the diameter of the fibers of the upper layer is from 3.5 to 10 denier. More preferably, the diameter of the fibers of the upper layer is from 4 to 8 denier.

The upper layer of the acquisition web 52 may comprise at least 50%, or at least 60%, or at least 70%, or at least 80% of multicomponent fibers, by total weight of the upper layer of the acquisition web 52.

The upper layer of the acquisition web 52 may comprise only multicomponent fibers.

Having a relatively high percentage of fibers with relatively high fiber diameter (e.g. from 3.5 to 10 denier) provides an upper layer of the acquisition web with a relatively high degree of porosity. The liquid bodily exudates may be easily absorbed from the topsheet 24 to the upper layer of the acquisition web 52 and within the acquisition web 52.

The upper layer may comprise fibers having a diameter from 0.8 to 2.5 denier. For example, the upper layer may not comprise more than 15% or more than 10% of fibers having a diameter from 0.8 to 2.5 denier by total weight of the upper layer. The upper layer may not comprise at all fibers having a diameter from 0.8 to 2.5 denier.

The Lower Layer of the Acquisition Web 52

The lower layer of the acquisition web 52 may comprise a mixture of a first type of fibers and of a second type of fibers.

Preferably, the diameter of the first type of fibers is from 3.5 to 10 denier. More preferably, the diameter of the first type of fibers is from 4 to 8 denier.

Preferably, the diameter of the second type of fibers is from 0.8 to 2.5 denier. More preferably, the diameter of the second type of fibers is from 1.0 to 2.0 denier.

The lower layer of the acquisition web 52 may comprise a mixture of first type of fibers having a diameter from 3.5 to 10 denier and of a second type of fibers having a diameter from 0.8 to 2.5 denier.

The second type of fibers may constitute at least 30%, preferably at least 40% of the total weight of the lower layer.

The second type of fibers may constitute not more than 50%, or not more than 45% of the total weight of the lower layer.

The first type of fibers may constitute at least 40%, preferably at least 50% of the total weight of the lower layer. The lower layer may not comprise more than 65%, or not more than 60% of a first type of fibers, of the total weight of the lower layer.

The diameter of the first type of fibers may be at least 50% larger or at least 60% larger or at least 80% larger, or at least 100% larger, or at least 200% larger than the diameter of the second type of fibers.

The first type of fibers and the second type of fibers may constitute at least 90%, preferably at least 95% of the total weight of the lower layer.

The lower layer of the acquisition web 52 may comprise from 60% to 80% of a first type of fibers and from 20% to 40% of a second type of fibers. Preferably, the lower layer of the acquisition web 52 comprises from 60% to 70% of a first type of fibers and from 30% to 40% of a second type of fibers.

The first type of fibers of the lower layer may be multicomponent fibers, such as core/sheath bicomponent fibers or side-by-side bicomponent fibers. Preferably, the first type of fibers of the lower layer are core/sheath bicomponent fibers.

The second type of fibers of the lower layer may be monocomponent fibers, such as multilobal monocomponent fibers, in particular trilobal monocomponent fibers. Preferably, the second type of fibers of the lower layer are multilobal monocomponent fibers such as trilobal monocomponent fibers.

The lower layer of the acquisition web 52 may be a mixture of different types of fibers, i.e. a mixture of monocomponent fibers and bicomponent fibers. The lower layer of the acquisition web 52 may consist of a mixture of bicomponent fibers and monocomponent fibers, such that the bicomponent fibers and the monocomponent fibers together form 100% of the total weight of the lower layer of the acquisition web 52.

The lower layer of the acquisition web 52 may comprise more than 30% of monocomponent fibers, preferably more than 40% of monocomponent fibers by total weight of the lower layer of the acquisition web 52 but not more than 50% of monocomponent fibers by total weight of the lower layer of the acquisition web 52.

The lower layer of the acquisition web 52 may comprise more than 50% of multicomponent fibers, preferably more than 60% of multicomponent fibers, but not more than 65% of multicomponent fibers by total weight of the lower layer of the acquisition web 52.

Having a certain amount of fibers with relatively small fiber diameter helps to increase overall opacity of the web, especially if the fibers such as multilobal (e.g. trilobal) fibers are used, given that non-round fibers have a higher ratio of fiber surface area to fiber volume. Therefore, increased opacity helps disguise the liquid bodily exudates absorbed within the absorbent article 20.

The Effect of the Upper Layer and the Lower Layer

The average diameter of the fibers in the upper layer of the acquisition web 52 is higher than the average diameter of the fibers in the lower layer of the acquisition web 52.

The ratio of the weight of the upper layer compared to the weight of the lower layer may range from 1:4 to 2.5:1, or from 1:2.5 to 2:1, or from 1:2 to 1:1.

The difference of fibers diameter between the upper layer and the lower layer of the acquisition web 52 create a capillary gradient within the acquisition web 52. This capillary gradient improves the dewatering of the topsheet 24 of the topsheet/acquisition web laminate 245. Thus, the topsheet/acquisition web laminate 245 can reduce the contact of liquid bodily exudates with the skin of the wearer. The fluid handling properties of the absorbent article 20 will be improved.

The upper layer and the lower layer of the acquisition web 52 may constitute at least 90%, preferably at least 95% of the total weight of the acquisition web 52.

Method of Making the Acquisition Web 52

The method of making the acquisition web 52 of the present invention comprises the steps of:

A layer of fibers of the upper layer is formed. Preferably, the fibers are formed by a carding process. The fibers are laid down on a conveyor belt or drum to form a layer of non-consolidated fibers. The layer is preferably laid down in form of a substantially endless layer. The layer of non-consolidated may be a homogeneous layer having substantially homogeneous basis weight. "Substantially homogeneous basis weight" is to be understood, in the sense that the basis weight may vary slightly due to process conditions, especially for relatively low basis weight fiber lay down; however; the basis weight is not varied intentionally throughout the layer of non-consolidated fibers. Alternatively, the basis weight may vary across CD and/or MD, i.e. the basis weight differs intentionally in CD and/or MD.

A layer of fibers of the lower layer is formed. The same process may be applied as described above.

In a subsequent method step, the layer of non-consolidated fibers of the upper layer is combined in a face to face relationship with the layer of non-consolidated fibers of the lower layer. The combined two layers of non-consolidated fibers are then subjected to air-through bonding. Air through bonders are described in more detail above. Due to the air-through bonding, the fibers within the upper layer and the lower layer and between the upper layer and the lower layer are autogenously bonded to each other. As a result of the air-through bonding, a consolidated nonwoven fibrous web, i.e. acquisition web 52 with relatively high loft is formed.

The acquisition web 52 may be wound up in roll form for storage or transport. Alternatively, the acquisition web 52 may be conveyed to a subsequent method step, such as a step whereby the web is incorporated into an absorbent article.

General Structure and Properties of the Topsheet/Acquisition Web Laminate 245

A topsheet/acquisition web laminate 245 having a three-dimensional structure is provided.

The absorbent article 20, described above, comprises an acquisition web 52 having a first and second surface. The first surface of the topsheet 24 will be facing towards the body of the wearer when the absorbent article 20 is in use.

The liquid permeable topsheet 24 and the acquisition web 52 are aligned in a face to face relationship such that the second surface of the topsheet 24 is in contact with the first surface of the acquisition web 52.

The absorbent article 20 comprises a topsheet/acquisition web laminate 245 which comprises the topsheet 24 and the acquisition web 52 in a face to face relationship. The topsheet/acquisition web laminate 245 comprises mechanical deformations forming three-dimensional protrusions 250 extending from a plane of the topsheet/acquisition web laminate 245.

The topsheet 24 and the acquisition web 52 may be in an intimate contact with each other.

According to a process detailed below, the topsheet 24 and the acquisition web 52 can be simultaneously mechanically deformed and combined together in a face to face relationship such to provide a topsheet/acquisition web laminate 245. This means that both topsheet 24 and acquisition web 52 can be mechanically deformed and combined together at the same time during the process.

Figure 7:
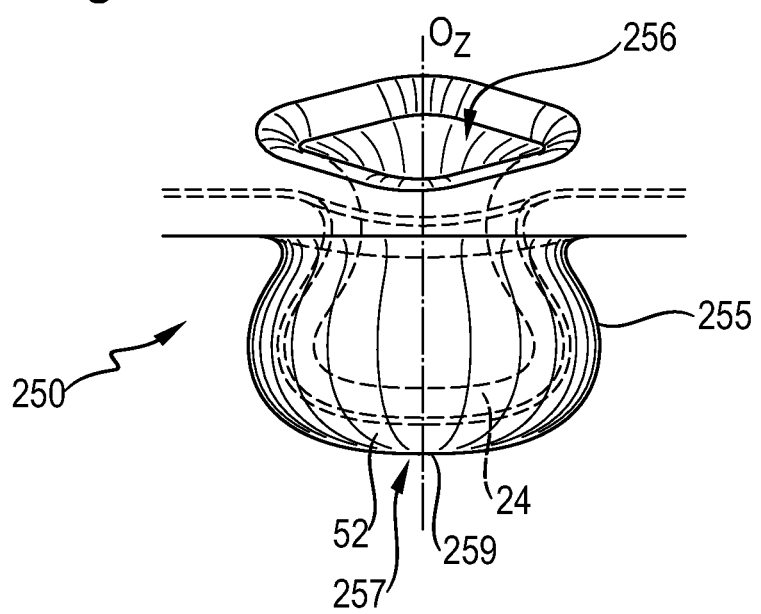
FIG. 7 is a perspective view of a three-dimensional protrusion of the topsheet/acquisition web laminate obtained with the apparatus shown in FIG. 8A.

Referring to FIG. 7, the three-dimensional protrusions 250 are formed from the fibers of the topsheet 24 and the acquisition web 52.

A majority of the three-dimensional protrusions 250 each may comprise a base 256 forming an opening, and having a measured protrusion base width according to the Measured Protrusion Base Width Test Method, an opposed distal portion 257, and one or more side walls 255 between the bases 256 and the distal portions 257 of the majority of the three-dimensional protrusions 250. The base 256, distal portion 257 and the one or more side walls 255 are formed by fibers such that the majority of the three-dimensional protrusions 250 have openings at the base 256, as shown in FIG. 7. The side wall 255 may be substantially continuous. For instance, the side wall 255 may be spherical or conical. The majority of the three-dimensional protrusion 250 may comprise more than one side wall 255, e.g. in a pyramidal-shaped protrusion. The fibers may substantially or completely surround the one or more side walls 255 of the three-dimensional protrusions 250.

At least 50% or at least 80% or at least 95% of the three-dimensional protrusions 250 of the topsheet/acquisition web laminate 245 may only have openings at the base. The majority of the three-dimensional protrusions 250 may comprise broken fibers. The majority of the three-dimensional protrusions may be obtained by the mechanical process described in detail below.

The fibers may substantially or completely surround the one or more side walls 255 of the majority of the three-dimensional protrusions 250. This means that there are multiple fibers which contribute to form a portion of the side walls 255 and distal portion 257 of a three-dimensional protrusion 250. The phrase "substantially surround" does not require that each individual fiber be wrapped substantially or completely around the side walls 255 of the majority of the three-dimensional protrusions 250.

The majority of the three-dimensional protrusions 250 of the topsheet/acquisition web laminate 245 may at least be present in the area where the topsheet 24 overlaps the acquisition web 52 in the topsheet/acquisition web laminate 245. However, the majority of the three-dimensional protrusions 250 of the topsheet/acquisition web laminate 245 may also be present in the topsheet 24 where the topsheet 24 does not overlaps the acquisition web 52. In that case, the majority of the three-dimensional protrusions 250 which are formed in the topsheet 24 of the topsheet/acquisition web laminate 245 are formed from the fibers of the topsheet 24.

In another alternative, the majority of the three-dimensional protrusions 250 of the topsheet/acquisition web laminate 245 may only be present where the topsheet 24 overlaps the acquisition web 52 in the topsheet/acquisition web laminate 245.

The three-dimensional protrusions 250 of the topsheet/acquisition web laminate 245 may have a measured protrusion height of at least 0.3 mm according to the Measured Protrusions Height Test Method as described below.

The three-dimensional protrusions 250 of the topsheet/acquisition web laminate 245 may have a measured protrusion height from 0.3 mm to 5 mm or from 0.7 mm to 3 mm or from 1.0 mm to 2.0 mm according to the Measured Protrusions Height Test Method as described below.

The three-dimensional protrusions 250 of the topsheet/acquisition web laminate 245 may have a measured protrusion base width of the three-dimensional protrusions 250 of at least 0.5 mm according to the Measured Protrusions Base Width Test Method as described below.

The three-dimensional protrusions 250 of the topsheet/acquisition web laminate 245 can have a measured protrusion base width of the three-dimensional protrusions 250 from 0.5 mm to 10 mm or from 0.5 mm to 5 mm or from 0.5 mm to 3.0 mm or from 1.0 mm to 2.5 mm or from 1.5 mm to 2.5 mm according to the Measured Protrusions Base Width Test Method as described below.

The three-dimensional protrusions 250 having a shape with a specific measured protrusion height and a measured protrusion base width can support the caregiver's perception that the absorbent article 20 is well able to absorb the liquid bodily exudates.

Maintenance or improvement of the dryness of the topsheet/acquisition web laminate 245 is evaluated by the amount of liquid in topsheet which is determined by the Liquid in Topsheet test method. The liquid in topsheet is the retained liquid bodily exudates in the topsheet 54 of the topsheet/acquisition web laminate 245 after the absorbent article 20 has acquired the liquid bodily exudates after a first gush.

The topsheet/acquisition web laminate 245 may have a liquid in topsheet value of less than 200 mg or less than 180 mg or less than 160 mg according to the liquid in topsheet test method.

The topsheet/acquisition web laminate 245 comprising the acquisition web with a capillary gradient can help obtaining reduced liquid in topsheet compared to the same absorbent article 20 comprising either a topsheet/acquisition web laminate forming three-dimensional protrusions with a classic acquisition web or either the same topsheet 24 overlaying the same acquisition web 52 without any mechanical deformations forming three-dimensional protrusions 250.

Moreover, the topsheet 24 and the acquisition web 52 in the topsheet/acquisition web laminate 245 may be in an intimate contact with each other. At the same time, the topsheet/acquisition web laminate 245 is in close contact with the underlaying layer, i.e. the optional distribution layer 54 or the absorbent core 28, which allows the liquid bodily exudates to flow from the topsheet 24 through the acquisition web 52 to the absorbent core 28 efficiently.

Furthermore, the topsheet/acquisition web laminate 245 comprises three-dimensional protrusions 250. The majority of the three-dimensional protrusions 250 provide therefore void volume inside the three-dimensional protrusions to acquire the liquid bodily exudates. Hence, the liquid bodily exudates can be transmitted more efficiently from the topsheet/acquisition web laminate 245 to the distribution layer 54. The void volumes 253 of the laminate 245 can allow feces to be absorbed and acquired within them. In that case, the present invention is suitable to absorb feces of relatively low viscosity.

A width of the acquisition web 52 in a direction parallel to the transversal axis 90 is less than a width of the topsheet 24 in a direction parallel to the transversal axis 90 of the absorbent article 20. If the width of both topsheet 24 and acquisition web 52 were the same, wicking of the liquid bodily exudates underneath the gasketing cuffs 32 might occur. Hence, the liquid bodily exudates might not be properly absorbed by the absorbent core 28, which may lead to leakage of the liquid bodily exudates out of the absorbent article. If the width of the acquisition web 52 in a direction parallel to the transversal axis 90 is less that the width of the topsheet 24 in a direction parallel to the transversal axis 90, the acquisition web 52, which may receive the liquid bodily exudates from the topsheet 24, can directly transmit the liquid bodily exudates to the optional distribution layer 54. Hence, the liquid bodily exudates temporary stored in the acquisition web 52 of the topsheet/acquisition web laminate 245 will not readily be drawn towards and underneath the gasketing cuffs 32 by capillary forces. Leakage can thus be reduced.

The width of the acquisition web 52 in a direction parallel to the transversal axis 90 of the topsheet/acquisition web laminate 245 may not be more than 40% wider than the width of the optional distribution layer 54 and/or more than 20% wider than the width of the absorbent core 28 in a direction parallel to the transversal axis 90. In that case, the liquid bodily exudates may not accumulate at or adjacent to the longitudinal edges of the acquisition web. Indeed, when the acquisition web 52 of the topsheet/acquisition web laminate 245 is no more than 20% wider than the width of the absorbent core 28, the liquid bodily exudates can readily be transported into the absorbent core 28, which can efficiently drain the fluid from the acquisition web 52 into the absorbent core 28.

A portion of the backsheet 25 may be joined to the topsheet 24 at or adjacent to the longitudinal edges of the first surface of the topsheet/acquisition web laminate 245 in the cross direction. The longitudinal edges of the first surface of the topsheet/acquisition web laminate 245 do not comprise any acquisition web 52. When a portion of the backsheet 25 is joined to a portion of the topsheet 24 of the topsheet/acquisition web laminate 245, the acquisition web 52 is then enveloped between the topsheet 24 and the backsheet 25.

The acquisition web 52 can receive the liquid bodily exudates that pass through the topsheet 24 and can distribute them to underlying absorbent layers. The topsheet 24 of the topsheet/acquisition web laminate 245 can be readily dewatered. The topsheet 24 in the topsheet/acquisition web laminate 245 may be less hydrophilic than the acquisition web 52.

The length of the acquisition web 52 in the topsheet/acquisition web laminate 245 in a direction parallel to the longitudinal axis may be less than the length of the topsheet 24 taken along the longitudinal axis 80 of the absorbent article 20, in a direction parallel to the longitudinal axis. When the length of the acquisition web 52 in the topsheet/acquisition web laminate 245 is less than the length of the topsheet 24, the liquid bodily exudates cannot be readily drawn towards the lateral edges 10, 12 of the absorbent article 20, which reduces leakage.

The length of the acquisition web 52 in the topsheet/acquisition web laminate 245 may be less than the length of the absorbent core 28 taken along the longitudinal axis 80 of the absorbent article 20.

The majority of the three-dimensional protrusions 250 of the topsheet/acquisition web laminate 245 may protrude generally towards the backsheet 25 of the absorbent article 20.

Having three-dimensional protrusions 250 of the topsheet/acquisition web laminate 245 protruding towards the backsheet 25 can help acquiring and absorbing the liquid bodily exudates to the absorbent core 28.

The topsheet 24 of the topsheet/acquisition web laminate 245 may be coated with a lotion composition. The lotion composition may be located in the areas of the topsheet 24 which are between the three-dimensional protrusions 250 of the topsheet/acquisition web laminate 245.

Typical lotion compositions used in diapers are disclosed in U.S. Pat. No. 6,426,444 B2. The resulting lotion composition may be applied to the topsheet/acquisition web laminate by spraying, printing (e.g., flexographic printing), coating (e.g., contact slot coating, gravure coating), extrusion, microencapsulation or combinations of these application techniques.

The majority of the three-dimensional protrusions 250 may be disposed in any suitable arrangement across the plane of the topsheet/acquisition web laminate 245.

The majority of the three-dimensional protrusions 250 of the topsheet/acquisition web laminate 245 may be provided in the complete surface of the topsheet/acquisition web laminate 245 or may only be provided in a portion of the surface of the topsheet/acquisition web laminate 245. Particularly, the three-dimensional protrusions 250 of the topsheet/acquisition web laminate 245 may be provided in an area of at least 30×40 mm of the surface of the topsheet/acquisition web laminate 245.

At least 10 three-dimensional protrusions 250 may be comprised by an area of at least 30×40 mm of the surface of the topsheet/acquisition web laminate 245.

An area of 10 cm2 of the topsheet/acquisition web laminate 245, may comprise from 5 to 100 three-dimensional protrusions 250, from 10 to 50 three-dimensional protrusions 250 or from 20 to 40 three-dimensional protrusions 250.

In the area where the three-dimensional protrusions 250 of the topsheet/acquisition web laminate 245 are provided, the three-dimensional protrusions 250 may be uniformly distributed.

Suitable arrangements include, but are not limited to: staggered arrangements, and zones. In some cases, the topsheet/acquisition web laminate 245 may comprise both three-dimensional protrusions 250 and other features known in the art such as embossments and apertures. The three-dimensional protrusions 250 and other features may be in separate zones, be intermixed, or overlap. Intermixed arrangements can be created in any suitable manner. In some cases, intermixed arrangements can be created by using the techniques described in U.S. Patent Publication No. U.S. Pat. Appl. Publ. No. 2012/0064298 A1, Orr, et al. In other cases, overlapping arrangements can be created by forming the three-dimensional protrusions 250 and then subsequently passing the topsheet/acquisition web laminate 245 between a forming member having male forming elements thereon and a compliant surface, and applying pressure to the web with the forming member and compliant surface. These techniques for producing overlapping arrangements enable three-dimensional protrusions 250 and other features to be combined so they are disposed in different locations on the topsheet/acquisition web laminate 245 or they can cause at least some of the three-dimensional protrusions 250 and at least some of the other features (apertures, embossments) to be disposed in the same location on the topsheet/acquisition web laminate 245.

The Mechanical Deformations of the Topsheet 24 and of the Acquisition Web 52

The topsheet 24 and acquisition web 52 may be joined together prior or during the mechanical deformation. If desired an adhesive, chemical bonding, resin or powder bonding, or thermal bonding between the topsheet 24 and acquisition web 52 may be selectively utilized to bond certain regions or all of the topsheet 24 and acquisition web 52 together. In addition, the topsheet 24 and acquisition web 52 may be bonded during processing, for example, by carding the topsheet 24 of onto the acquisition web 52 and thermal point bonding the combined layers.

Prior to any mechanical deformation, the topsheet 24 may be attached to the acquisition web 52. For instance, the topsheet 24 may be attached to the acquisition web 52 where the topsheet 24 and acquisition web 52 overlaps. The attachment of the topsheet 24 to the acquisition web 52 may include a uniform continuous layer of adhesive, a discontinuous patterned application of adhesive or an array of separate lines, spirals, or spots of adhesive.

The basis weight of the adhesive in the topsheet/acquisition web laminate 245 may be from 0.5 to 30 gsm or from 1 to 10 gsm or from 2 to 5 gsm.

Figure 8C:
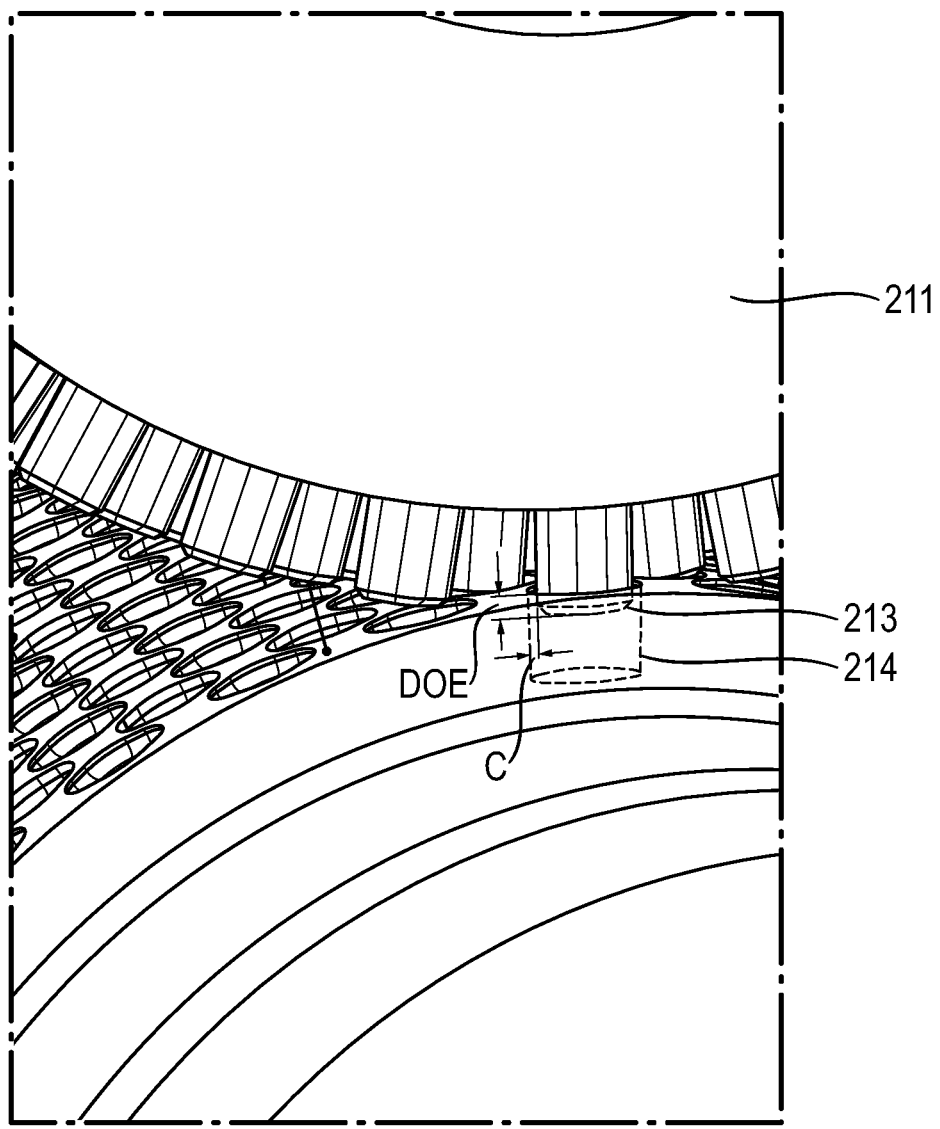
FIG. 8C is a perspective view of the apparatus shown in FIG. 8A, showing the first forming member intermeshing the second forming member.

As exemplified in FIGS. 8A, 8B and 8C, the topsheet 24 and the acquisition web 52 may be engaged together between a first and second forming members 211, 212 and be simultaneously mechanically deformed and combined together to form the topsheet/acquisition web laminate 245. The topsheet/acquisition web laminate 245 comprises thus deformations forming three-dimensional protrusions 250.

The first and second forming member 211, 212 may be drum-shaped, generally cylindrical as shown in FIGS. 8A, 8B and 8C, or plate-shaped.

The first forming member 211 of the apparatus 200 may have a surface comprising a plurality of discrete, spaced apart male forming elements 213 having a base that is joined to the first forming member 211, a top that is spaced away from the base, and sides that extend between the base and the top of the male forming elements 213. The male forming elements 213 may have a plan view periphery, and a height.

The top on the male forming elements 213 may have a rounded diamond shape, see for example FIG. 8B, with vertical sidewalls and a radiused or rounded edge at the transition between the top and the sidewalls of the male forming element 213.

The second forming member 212 may have a surface comprising a plurality of recesses 214 in the second forming member 212. The recesses 214 may be aligned and configured to receive the respective male forming elements 213 therein. Hence, each recess 214 of the second forming member 212 may be sufficiently large to be able to receive each respective male forming element 213 of the first forming member 211. The recesses 214 may have a similar shape as the male forming elements 213. The depth of the recesses 214 may be greater than the height of the male forming elements 213.

The first and second forming member 211, 212 may be further defined by a depth of engagement (DOE) which is a measure of the level of intermeshing of the first and second forming member 211, 212, as shown in FIG. 8C. The depth of engagement (DOE) may be measured from the tip of the male forming elements 213 to the outermost portion of the surface of the second forming member 212 which portions are not within a recess 214. The depth of engagement (DOE) may range from 1.5 mm to 5.0 mm or from 2.5 mm to 5.0 mm or from 3.0 mm to 4.0 mm.

The first and second forming member 211, 212 may be defined by a clearance between the first and second forming member 211, 212 as shown in FIG. 8C. The clearance is the distance between the side wall of the male forming element 213 and the side wall of the recess 214. The clearance may range from 0.1 mm to 2 mm or from 0.1 mm to 1.5 mm from 0.1 mm to 1 mm.

The topsheet 24 and the acquisition web 52 may be therefore engaged together between the first and second forming members 211, 212 and be mechanically deformed and combined together to form the topsheet/acquisition web laminate 245. The topsheet/acquisition web laminate 245 comprises mechanical deformations forming three-dimensional protrusions 250.

The topsheet/acquisition web laminate 245 may comprise the majority of the three-dimensional protrusions 250 having different shapes.

Viewed from a cross-sectional view, i.e. in a Z-direction, the majority of the three-dimensional protrusions 250 may have any suitable shapes which include, but are not limited to: bulbous-shaped, conical-shaped and mushroom shaped.

Viewed from above, the majority of the three-dimensional protrusions 250 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the three-dimensional protrusions 250 may be non-circular.

The majority of the three-dimensional protrusions 250 may form, in conjunction, one or more graphics. Having graphics can support the caregiver's perception that the absorbent article is well able to absorb the liquid bodily exudates.

Also, the majority of the three-dimensional protrusions 250 may form, in conjunction, one or more graphics such as a logo, e.g. the Pampers Heart logo.

The Resulting Three-dimensional Protrusions

The majority of the three-dimensional protrusions 250 may have similar plan view dimensions in all directions, or the majority of the three-dimensional protrusions 250 may be longer in one dimension than another. The majority of the three-dimensional protrusions 250 may have different length and protrusion base width dimensions. The majority of the three-dimensional protrusions 250 may, thus, have a ratio of length to protrusion base width. The ratio of length to protrusion base width can range from 10:1 to 1:10.

The topsheet/acquisition web laminate 245 may comprise a plurality of three-dimensional protrusions 250 which extend towards the distribution layer 54.

When the majority of the three-dimensional protrusions 250 extend towards the distribution layer 54, the area of contact between the acquisition web 52 of the topsheet/acquisition web laminate 245 and the underneath distribution layer 54 is improved. The distribution layer 54 will follow the shape of the majority of the three-dimensional protrusions 250. Hence, the transfer of the liquid bodily exudates from the topsheet/acquisition web laminate 245 to the distribution layer 54 can be increased.

Referring to FIG. 7, a bulbous-shaped protrusion may be one type of three-dimensional protrusions 250 which may be obtained by the process described above using the apparatus 200. The topsheet/acquisition web laminate 245 may comprise the majority of the three-dimensional protrusions 250 extending towards the backsheet 25.

Figure 9:
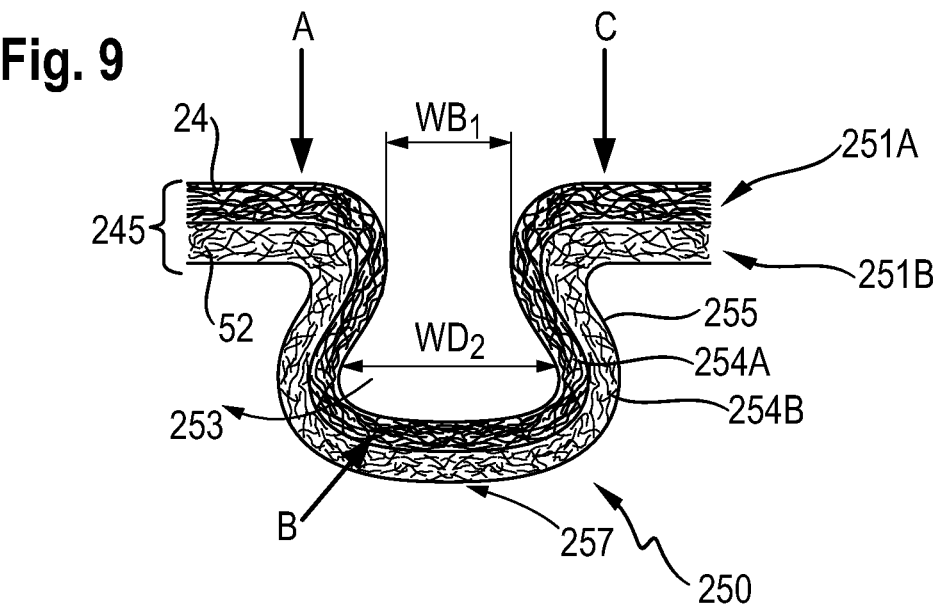
FIG. 9 is a schematic view of a three-dimensional protrusion of the topsheet/acquisition web laminate obtained with the apparatus shown in FIG. 8A.

As shown in FIG. 9, a three-dimensional protrusion 250 comprising an inner and outer three-dimensional protrusion 251A and 251B may be made from engaging the topsheet 24 with the acquisition web 52 between the first and second forming member 211, 212 such as the inner three-dimensional protrusion 251A from the topsheet 24 and the outer three-dimensional protrusion 251B from the acquisition web 52 coincide with and fit together. Hence, as shown in FIG. 9, the inner three-dimensional protrusion 251A of the topsheet 24 and the outer three-dimensional protrusion 251B of the acquisition web 52 are nested together.

The inner three-dimensional protrusion 251A may comprise a plurality of fibers 254A which constitutes the topsheet 24. The outer three-dimensional protrusion 251B in which the inner three-dimensional protrusion 251A may be nested, may comprise a plurality of fibers 254B which constitutes the acquisition web 52. The plurality of fiber 254A, 254B composing the three-dimensional protrusion 250 may surround the side walls 255 of the three-dimensional protrusions 250.

The topsheet 24 and the acquisition web 52 may be both extensible, i.e. the fibers composing the topsheet 24 and acquisition web 52 may be able to elongate and/or may be mobile, such that the topsheet 24 and acquisition web 52 are able to stretch to be nested together.

Generally, the extensibility of the materials composing the topsheet 24 and acquisition web 52 can be selected according to the desired sizes of the three-dimensional protrusions 250. If relatively large three-dimensional protrusions 250 are desired, materials with a relatively higher extensibility will be chosen.

For instance, the topsheet 24 or acquisition web 52 may be capable of undergoing an apparent elongation of equal to or greater than at least 100% or 110% or 120% or 130% up to 200% in the machine and/or cross-machine directions at or before reaching the breaking force according to the Test Method as set out in the Definition part.

In some cases, it might be desired to have the majority of the three-dimensional protrusions 250 which are larger either in the machine or cross-machine direction. For this, the materials composing the topsheet 24 and acquisition web 52 can be thus relatively more extensible either along the longitudinal axis versus the transversal axis of the absorbent article or vice versa.

Due to the mechanical deformation of the laminate 245, the fibers of the acquisition web 52 may be shifted from the opposite distal portion 257 of the three-dimensional protrusions 250 to the side walls 255 of the three-dimensional protrusions 250 and in particular to the land areas between each three-dimensional protrusions 250. The permeability of liquid bodily exudates through the laminate 245 can be improved.

The majority of the three-dimensional protrusion 252 may comprise a void volume 253 which is the portion of the three-dimensional protrusion 251A which does not comprise any fibers or very little fibers. The majority of the three-dimensional protrusion 250 may be defined by a protrusion base width WB1 of the base 256 forming an opening which is measured from two side walls of the inner portion 251A at the base 256. The majority of the three-dimensional protrusion 250 may be defined by a width WD2 of the void volume 253 which is the maximum interior width measured between two side walls of the inner three-dimensional protrusion 251A or which is the maximum diameter of the side wall of the inner three-dimensional protrusion 251A when the distal portion has a substantially circular shape. The maximum interior width WD2 of the void volume 253 at the distal portion may be greater than the protrusion base width WB1 of the base 256 of the three-dimensional protrusion 250. The protrusion base width WB1 of the base 256 of the majority of the three-dimensional protrusion 250 may range from 1.5 mm to 15 mm or from 1.5 mm to 10 mm or from 1.5 mm to 5 mm or from 1.5 mm to 3 mm. Measurements of the dimensions of the protrusion base width WB1 of the base 256 and the width WD2 of the distal portion 257 can be made on a photomicrograph. When the size of the protrusion base width WB1 of the base 256 is specified herein, it will be appreciated that if the openings are not of uniform width in a particular direction, the protrusion base width, WB1, is measured at the widest portion. Measurements of the protrusion base width WB1 of the base 256 or the maximum interior width WD2 of the void volume 253 at the distal portion 257 can be made on a photomicrograph at 20× magnification.

Preferably, the ratio of the circumference length of the three-dimensional protrusions 250 to the length of the opening at the base 256 is less than 4:1.

To measure the circumference length of the three-dimensional protrusions 250, the laminate 245 comprising the three-dimensional protrusions is arranged so that the viewing direction is co-linear with the longitudinal axis (MD) of the three-dimensional protrusions. If necessary, a cross-section of the three-dimensional protrusions 250 can be obtained by cutting the three-dimensional protrusions perpendicular to the longitudinal axis using sharp scissors or a razor blade, taking care in preserving the overall geometry of the three-dimensional protrusions while cutting it.

As shown in FIG. 9, the circumference length of the three-dimensional protrusions 250 are measured and recorded by starting the measurement at a first origination point A, proceeding along the side walls 255 of the three-dimensional protrusions 250 to the distal portion 257 of the three-dimensional protrusions 250 at a second point B (along the median path of the fibers) and terminating the measurement at the third origination point C. The length of the opening at the base 256 is measured and recorded parallel to the plane of the laminate 245 between the first origination point A and the third origination point C. The circumference length of the three-dimensional protrusions 250 are measured where the three-dimensional protrusions 250 are not under any pressure or strain.

As the plurality of fiber 254A, 254B composing the majority of the three-dimensional protrusions 250 may be present in the one or more side walls 255 of the majority of the three-dimensional protrusions 250, the majority of the three-dimensional protrusions may not collapse on one side and close off the opening at the base 256 when compressive forces are applied on the topsheet/acquisition web laminate 245. The opening at the base 256 may be maintained and may create a ring of increased opacity around the opening at the base 256 when the three-dimensional protrusion 250 has been compressed. Hence, the majority of the three-dimensional protrusion 250 can be preserved and remain visible to the consumer when viewing the absorbent article 20 from the topsheet 24. The majority of the three-dimensional protrusion 250 can be preserved after being subjected to any inherent compressive forces due to the process or the step of compressing the absorbent articles comprising the topsheet/acquisition web laminate 245 prior to be filled in a packaging.

In other words, the majority of the three-dimensional protrusions 250 may have a degree of dimensional stability in the X-Y plane when a Z-direction force is applied to the majority of the three-dimensional protrusions 250. It is not necessary that the collapsed configuration of the majority of the three-dimensional protrusions 250 be symmetrical, only that the collapsed configuration prevent the majority of the three-dimensional protrusions 250 from flopping over or pushing back into the original plane of the topsheet/acquisition web laminate 245. Without wishing to be bound to any particular theory, the wide base 256 and large cap 52 (greater than the protrusion base width of the base opening 44), combined with the lack of a pivot point, causes the three-dimensional protrusions 250 to collapse in a controlled manner (the large distal portion 257 prevents the three-dimensional protrusion 250 from flopping over and pushing back into the original plane of the topsheet/acquisition web laminate 245). Thus, the majority of the three-dimensional protrusions 250 are free of a hinge structure that would otherwise permit them to fold to the side when compressed.

It may be desirable for at least one of the three-dimensional protrusions 250 in the topsheet/acquisition web laminate 245 to collapse in a controlled manner described below under the 7 kPa load when tested in accordance with the Accelerated Compression Method in the Test Methods section below.

Alternatively, at least some, or in other cases, a majority of the three-dimensional protrusions 250 may collapse in the controlled manner described herein.

Alternatively, substantially all of the three-dimensional protrusions 250 may collapse in the controlled manner described herein. The ability of the three-dimensional protrusions 250 to collapse may also be measured under a load of 35 kPa, 7 kPa, 4 kPa or 1 kPa. The 1 kPa, 4 kPa, 7 kPa and 35 kPa loads simulate manufacturing and compression packaging conditions. Wear conditions can range from 2 kPa or less up to 7 kPa.

Generally, the majority of the three-dimensional protrusions 250 may be configured to collapse in a controlled manner such that each base 256 forming an opening remains open, and the protrusion base width of each base 256 forming an opening is greater than 0.5 mm after compression.

In the area of the three-dimensional protrusions 250, the topsheet 24 and/or acquisition web 52 may comprise one or more interruptions. The formation of the one or more interruptions may be due to the properties of the topsheet 24 and acquisition web 52. The topsheet 24 may be less extensible with regard to fiber mobility and/or fiber extensibility than the acquisition web 52 or vice versa such that an interruption starts to form in the topsheet 24 and/or acquisition web 52.

Generally, the acquisition web 52 may have a lower extensibility than the topsheet 24. In such cases, the acquisition web 52 may start to rupture and form an interruption, i.e. the fibers composing the acquisition web 52 may be less extensible and/or mobile than the fibers composing the topsheet 24.

The interruptions may be formed by locally rupturing the acquisition web 52 and/or the topsheet 24 by the process described in detail above.

Generally, the topsheet 24 may have a lower extensibility than the acquisition web 52. In such cases, the topsheet 24 may start to rupture and form an interruption, i.e. the fibers composing the topsheet 24 may be less extensible and/or mobile than the fibers composing the acquisition web 52.

Fiber Concentration

The topsheet 24 may comprise a generally planar first region of the topsheet 24. The acquisition web 52 may comprise a generally planar first region of the acquisition web 52. The three-dimensional protrusions 250 of the respective topsheet 24 and the acquisition web 52 may comprise a plurality of discrete integral second regions. The term "generally planar" is not meant to imply any particular flatness, smoothness, or dimensionality. Thus, the first region of the topsheet 24 can include other features that provide the first region of the topsheet 24 with a topography. The first region of the acquisition web 52 can include other features that provide the first region of the acquisition web 52 with a topography. Such other features can include, but are not limited to small protrusions, raised network regions around the base 256 forming an opening, and other types of features. Thus, the first region of the topsheet 24 and/or the first region of the acquisition web 52 can be generally planar when considered relative to the respective second regions. The first region of the topsheet 24 and/or the first region of the acquisition web 52 can have any suitable plan view configuration. In some cases, the first region of the topsheet 24 and/or the first region of the acquisition web 52 can be in the form of a continuous inter-connected network which comprises portions that surround each of the three-dimensional protrusions 250.

The side walls 259 and the area around the base 256 of the majority of the three-dimensional protrusions 250 may have a visibly significantly lower concentration of fibers per given area (which may be evidence of a lower basis weight or lower opacity) than the portions of the topsheet 24 and/or the acquisition web 52 in the unformed first region of the respective topsheet 24 and the acquisition web 52. The majority of the three-dimensional protrusions 250 may also have thinned fibers in the side walls 259. Thus, the fibers may have a first cross-sectional area when they are in the undeformed topsheet 24 and the acquisition web 52, and a second cross-sectional area in the side walls 259 of the majority of the three-dimensional protrusions 250 of the topsheet/acquisition web laminate 245, wherein the first cross-sectional area is greater than the second cross-sectional area. The side walls 259 may also comprise some broken fibers as well. The side walls 259 may comprise greater than or equal to about 30%, alternatively greater than or equal to about 50% broken fibers.

As used herein, the term "fiber concentration" has a similar meaning as basis weight, but fiber concentration refers to the number of fibers/given area, rather than g/area as in basis weight.

The topsheet/acquisition web laminate 245 may comprise the majority of the three-dimensional protrusions 250 which are oriented with the base 256 facing upward in which the concentration of fibers at the distal end 259 of each respective topsheet 24 and the acquisition web 52 differs between the topsheet 24 and the acquisition web 52.

The concentration of fibers in the first region of the acquisition web 52 and in the distal ends 259 of the majority of the three dimensional protrusions 250 may be greater than the concentration of fibers in the side walls 255 of the majority of the three dimensional protrusions 250 in the acquisition web 52

The concentration of fibers in the first region of the topsheet 24 and in the distal ends 259 of the majority of the three dimensional protrusions 250 may be greater than the concentration of fibers in the side walls 255 of the majority of the three-dimensional protrusions 250 in the topsheet 24.

Alternatively, the concentration of fibers in the first region of the acquisition web 52 may be greater than the concentration of fibers in the side walls 255 of the majority of the three-dimensional protrusions 250 in the acquisition web 52, and the concentration of fibers in the side walls 255 of the majority of the three-dimensional protrusions 250 in the acquisition web 52 may be greater than the concentration of fibers forming the distal ends 259 of the majority of the three-dimensional protrusions 250 in the acquisition web 52.

The concentration of fibers in the first region of the acquisition web 52 may be greater than the concentration of fibers in the distal ends 259 of the majority of the three dimensional protrusions 250 in the acquisition web 52, and the concentration of fibers in the first region of the topsheet 24 and the distal ends 259 of the majority of the three dimensional protrusions 250 may be greater than the concentration of fibers in the side walls 255 of the majority of the three dimensional protrusions 250 in the topsheet 24.

A portion of the fibers that form the first region fibers in the acquisition web 52 and/or the topsheet 24 may comprise thermal point bonds, and the portion of the fibers in the acquisition web 52 and/or the topsheet 24 forming the side walls 255 and distal ends 259 of the majority of the three-dimensional protrusions 250 may be substantially free of thermal point bonds. In at least some of the three-dimensional protrusions, at least some of the fibers in the acquisition web 52 and/or the topsheet 24 may form a nest or circle around the perimeter of the three-dimensional protrusion 250 at the transition between the side wall 255 and the base 256 of the three-dimensional protrusion 250.

In some cases, the topsheet 24 or the acquisition web 52 may have a plurality of bonds (such as thermal point bonds) therein to hold the fibers together. Any such bonds are typically present in the precursor materials from which the respective topsheet 24 or the acquisition web 52 is formed.

Forming three-dimensional protrusions 250 in the topsheet/acquisition web laminate 245 may also affect the bonds (thermal point bonds) within the topsheet 24 and/or the acquisition web 52.

The bonds within the distal end 259 of the three-dimensional protrusions 250 may remain intact (not be disrupted) by the mechanical deformation process that formed the three-dimensional protrusions 250. In the side walls 255 of the three-dimensional protrusions 250, however, the bonds originally present in the precursor topsheet 24 and/or the acquisition web 52 may be disrupted. When it is said that the bonds may be disrupted, this can take several forms. The bonds can be broken and leave remnants of a bond. In other cases, such as where the precursor materials of the respective topsheet 24 or the acquisition web 52 is underbonded, the fibers can disentangle from a lightly formed bond site (similar to untying a bow), and the bond site will essentially disappear. In some cases, after the mechanical deformation process, the side walls 255 of the majority of the three-dimensional protrusions 250 may be substantially free (or completely free) of thermal point bonds.

The bonds within the first region of the topsheet 24 and the distal end 259 of the three-dimensional protrusions 250 may remain intact. In the side walls 255 of the three-dimensional protrusions 250, however, the bonds originally present in the precursor topsheet 24 may be disrupted such that the side walls 255 are substantially free of thermal point bonds. Such a topsheet 24 could be combined with an acquisition web 52 in which the concentration of fibers within the topsheet 24 in the first region and the distal end 259 of the three-dimensional protrusions 250 is also greater than the concentration of fibers in the side walls 255 of the three-dimensional protrusions 250.

The acquisition web 52 may have thermal point bonds within the first region of the acquisition web 52 and the distal end 259 of the three-dimensional protrusions 250 that remain intact. In the side walls 255 of the three-dimensional protrusions 250, however, the bonds originally present in the precursor acquisition web 52 comprising the acquisition web 52 may be disrupted such that the side walls 255 of the acquisition web 52 are substantially free of thermal point bonds. In other cases, the thermal point bonds in the acquisition web 52 at the distal end 259 of the three-dimensional protrusions 250 may also be disrupted so that the distal end 259 of at least some of the three-dimensional protrusions 250 are substantially or completely free of thermal point bonds.

EXAMPLES

Prototype Diaper for the Example:

Diaper prototypes are produced using Pampers New Baby S2 (size 2) diaper commercially available in Germany in year 2014 by first removing the commercial topsheet, acquisition layer and distribution layer in these diapers and inserting the topsheet/acquisition web laminate and the carrier layer/distribution layer laminate.

An hot melt adhesive is applied on the side of the diaper core and the carrier layer/distribution layer composite is placed with the distribution layer side facing the core on top of it, so that the edge of the carrier layer is 40 mm from the diaper chassis front edge with respect to the MD and centered with respect to the CD direction.

An hot melt adhesive is applied on the side of the distribution layer and the topsheet/acquisition web laminate is placed with the acquisition web side facing the distribution layer on top of it, so that the edge of the acquisition web is 40 mm from the diaper chassis front edge with respect to MD and centered with respect to CD direction.

Those diapers are compacted in a bag at an In Bag Stack Height, i.e. the total caliper of 10 bi-folded diapers, of 90 mm for 1 week, and the diapers have been conditioned at least 24 hours prior to any testing at 23° C.+/−2° C. and 50%+/−10% Relative Humidity (RH).

The topsheet of the topsheet/acquisition web laminate is a hydrophilic coated bi-component PP/PE (polypropylene/polyethylene) nonwoven material, with PP (polypropylene) core and PE (polyethylene) sheath. The bi-component PP/PE nonwoven material for the topsheet has an overall basis weight of 20 gsm. The bi-component PP/PE nonwoven material is first coated with a finish made of a fatty acid polyethylene glycol ester for the production of a permanent hydrophilic bi-component PP/PE nonwoven material. The topsheet of the topsheet/acquisition web laminate has a width of 156 mm and a length of 400 mm.

The carrier layer of the carrier layer/distribution layer laminate is a hydrophilically coated PP (polypropylene) nonwoven material, composed of two spunlaid and two meltblown layers (SMMS). The basis weight of the carrier layer is 8 gsm. The material is consolidated and thermopoint-bonded, then it is coated with a finish made of a mixture of cationic surfactants to render the carrier layer hydrophilic. The carrier layer has a width of 105 mm and a length of 259 mm.

The distribution layer of the carrier layer/distribution layer laminate is composed of intra-fiber crosslinked cellulose fibers, polyacrylic acid was used as cross-linking agent. The distribution layer has a basis weight of 200 gsm. The distribution layer has a width of 80 mm and a length of 239 mm.

The distribution layer and carrier layer are attached to each other with a hot melt adhesive applied in form of spirals with a basis weight of 2.2 gsm, the distribution layer is centered in MD and CD with respect to the carrier layer.

The acquisition web used is different for each example.

The acquisition web of the topsheet/acquisition web laminate for each example has a width of 90 mm and a length of 300 mm.

The topsheet and acquisition web of each example are attached to each other with a hot melt adhesive applied in form of spirals with a basis weight of 5 gsm. The topsheet/acquisition web laminate and the carrier layer/distribution layer laminate are attached to each other with a hot melt adhesive applied in form of spirals with a basis weight of 5 gsm. The acquisition web is placed 40 mm from the topsheet front edge with respect to MD and centered with respect to CD direction.

The topsheet and acquisition web attached together are simultaneously mechanically deformed by passing them between a pair of intermeshing male and female rolls. The protrusions are created such that the bases of the protrusions are present on the topsheet side (i.e. protrusions oriented towards the garment). The teeth on the male roll have a rounded diamond shape like that shown in FIG. 8A and FIG. 8B, with vertical sidewalls. The teeth are 3.38 mm (0.133 inch) long and 2.77 mm (0.109 inch) wide with a CD spacing of 5.08 mm (0.200 inch) and an MD spacing of 8.79 mm (0.346 inch). The recesses in the mating female roll also have a rounded diamond shape, similar to that of the male roll, with a clearance between the rolls of 0.53-1.09 mm (0.021-0.043 inch). The process speed is 200 diapers per minutes and depth of engagement (DOE) is 3.43 mm (0.135 inch), with the topsheet being in contact with the male roll and the acquisition web being in contact with the female roll.

Example 1

The acquisition web of the topsheet/acquisition web laminate according to the invention consists of:
  an upper layer consisting of 6 denier solid round coPET/PET concentric sheath/core bicomponent fibers (i.e. sheath made of polyethylene terephthalate and core made of polyethylene terephthalate);
  a lower layer consisting of a mixture of 6 denier solid round coPET/PET concentric sheath/core bicomponent fibers (i.e. sheath made of polyethylene and core made of polyethylene terephthalate) and 1.2 denier solid trilobal PET monocomponent fibers. The mixture consists of 60% of bicomponent fibers and 40% of trilobal monocomponent fibers by total weight of the lower layer.

The bicomponent fibers are commercially available from FiberVisions Corp. under the name ETC267CG3. The monocomponent fibers are commercially available from Kilop USA Inc. under the name Tarilin Nan Ya Y01. The fibers of the upper layer and the lower layer of the acquisition web have been laid down by a carding process and undergone an air-through bonding step.

Comparative Example 1

The comparative absorbent article 1 comprises an acquisition web consisting of a mixture of 6 denier solid round coPET/PET concentric sheath/core bicomponent fibers (i.e. sheath made of polyethylene terephtalate and core made of polyethylene terephthalate) and 1.2 denier solid trilobal PET monocomponent fibers (60 gsm). The mixture consists of 80%, by total weight of bicomponent fibers and 20%, by total weight of trilobal monocomponent fibers.

The bicomponent fibers are commercially available from FiberVisions Corp. under the name ETC267CG3. The monocomponent fibers are commercially available from Kilop USA Inc. under the name Tarilin Nan Ya Y01. The fibers of the acquisition web have been laid down by a carding process and undergone an air-through bonding step.

The comparative absorbent article 1 is different from example 1 by the structure and the composition of the acquisition web.

Comparative Example 2

The comparative absorbent article 2 comprises an acquisition web consisting of:
  an upper layer consisting of a mixture of 6 denier solid round coPET/PET concentric sheath/core bicomponent fibers (i.e. sheath made of polyethylene and core made of polyethylene terephthalate) and 1.2 denier solid trilobal PET monocomponent fibers (total represents 40 gsm). The mixture consists of 60% of bicomponent fibers and 40% of trilobal monocomponent fibers by total weight of the upper layer;
  a lower layer consisting of 6 denier solid round coPET/PET concentric sheath/core bicomponent fibers (i.e. sheath made of polyethylene terephthalate and core made of polyethylene terephthalate) (20 gsm).

The bicomponent fibers are commercially available from FiberVisions Corp. under the name ETC267CG3. The monocomponent fibers are commercially available from Kilop USA Inc. under the name Tarilin Nan Ya Y01. The fibers of the upper layer and the lower layer of the acquisition web have been laid down by a carding process and undergone an air-through bonding step.

The comparative absorbent article 2 is different from example 1 by the structure of the acquisition web.

Results:

The liquid in topsheet has been measured, according to the Liquid in Topsheet test method disclosed below, for the absorbent article according to the invention and for the comparative absorbent articles 1 and 2.

| | Liquid in Topsheet (mg) |
|---|---|
| Example 1 | 160 |
| Comparative example 1 | 208 |
| Comparative example 2 | 213 |

The data show that the topsheet/acquisition web laminate according to the invention has a liquid in topsheet value that is less than the value of the liquid in topsheet for the topsheet/acquisition web laminate of comparative examples 1 and 2. Thus, the capillary gradient created within the acquisition web according to the invention may improve the dewatering of the topsheet of the topsheet/acquisition web laminate, compared to comparative absorbent articles that do not have the same acquisition web.

The opacity has also been measured, according to the opacity test method disclosed below, for the absorbent article according to the invention and for the comparative absorbent articles 1.

| | Opacity (in %) |
|---|---|
| Example 1 | 67 (+/−2.20) |
| Comparative example 1 | 61 (+/−2.24) |

The opacity of the absorbent article according to the invention is better than the opacity for the absorbent comparative example. Having fibers of small diameter within the acquisition web, facing towards the absorbent core may increase the opacity of the acquisition web of the topsheet/acquisition web laminate.

Test Methods

Unless indicated otherwise, all tests described herein are made with samples conditioned at least 24 hours at 23° C.+/−2° C. and 50%+/−10% Relative Humidity (RH).

Measured Protrusion Base Width and Measured Protrusion Height Test Methods

1) General Information

The Measured Protrusion Base Width and Measured Protrusion Height of the three-dimensional protrusions of the topsheet/acquisition web laminate of an absorbent article are measured using a GFM Primos Optical Profiler instrument commercially available from GFMesstechnik GmbH, Warthestraβe 21, D14513 Teltow/Berlin, Germany. Alternative suitable non-touching surface topology profilers having similar principles of measurement and analysis, can also be used, here GFM Primos is exemplified.

The GFM Primos Optical Profiler instrument includes a compact optical measuring sensor based on a digital micro mirror projection, consisting of the following main components:

a) DMD projector with 800×600 direct digital controlled micro-minors
b) CCD camera with high resolution (640×480 pixels)
c) Projection optics adapted to a measuring area of at least 30×40 mm
d) Recording optics adapted to a measuring area of at least 30×40 mm
e) A table tripod based on a small hard stone plate
f) A cold light source (an appropriate unit is the KL 1500 LCD, Schott North America, Inc., Southbridge, Mass.)
g) A measuring, control, and evaluation computer running ODSCAD 6.3 software Turn on the cold-light source. The settings on the cold-light source are set to provide a color temperature of at least 2800K.

Turn on the computer, monitor, and open the image acquisition/analysis software. In the Primos Optical Profiler instrument, select "Start Measurement" icon from the ODSCAD 6.3 task bar and then click the "Live Image button".

The instrument is calibrated according to manufacturer's specifications using calibration plates for lateral (X-Y) and vertical (Z). Such Calibration is performed using a rigid solid plate of any non-shiny material having a length of 11 cm, a width of 8 cm and a height of 1 cm. This plate has a groove or machined channel having a rectangular cross-section, a length of 11 cm, a width of 6.000 mm and an exact depth of 2.940 mm. This groove is parallel to the plate length direction. After calibration, the instrument must be able to measure the width and depth dimensions of the groove to within ±0.004 mm.

All testing is performed in a conditioned room maintained at 23±2° C. and 50+/−10% relative humidity. The surface to be measured may be lightly sprayed with a very fine white powder spray. Preferably, the spray is NORD-TEST Developer U 89, available from Helling GmbH, Heidgraben, Germany.

2) Measured Protrusion Base Width Test Method

The topsheet/acquisition web laminate is extracted from the absorbent article by attaching the absorbent article to a flat surface in a taut planar (i.e. stretched planar) configuration with the topsheet of the topsheet/acquisition web laminate facing up. Any leg or cuff elastics are severed in order to allow the absorbent article to lie flat. Using scissors, two longitudinal cuts are made through all layers above the absorbent core (i.e. the core wrap) along the edges of the topsheet/acquisition web laminate. Two transversal cuts are made through the same layers following the front and back waist edges of the absorbent article.

The topsheet/acquisition web laminate and any other layers above the absorbent core are then removed without perturbing the topsheet/acquisition web laminate. Freeze spray (e.g. CRC Freeze Spray manufactured by CRC Industries, Inc. 885 Louis Drive, Warminster, Pa. 18974, USA), or equivalent aid may be used to facilitate removal of the uppermost layers from the absorbent article. The topsheet/acquisition web laminate is then separated from any other layers, including any carrier layer (e.g. a nonwoven carrier layer, a tissue layer), using freeze spray if necessary. If a distribution layer, e.g. a pulp containing layer is attached to the topsheet/acquisition web laminate, any residual cellulose fibers are carefully removed with tweezers without modifying the acquisition web.

The topsheet/acquisition web laminate with three-dimensional protrusions (conditioned at a temperature of 23° C.±2° C. and a relative humidity of 50%±10% for at least 24 hours) namely "the specimen" is laid down on a hard flat horizontal surface with the body-facing side upward, i.e. the topsheet of the topsheet/acquisition web laminate being upward. Ensure that the specimen is lying in planar configuration, without being stretched, with the specimen uncovered.

A nominal external pressure of 1.86 kPa (0.27 psi) is then applied to the specimen. Such nominal external pressure is applied without interfering with the topology profile measurement. Such an external pressure is applied using a transparent, non-shining flat Plexiglas® plate 200 mm by 70 mm and appropriate thickness (approximately 5 mm) to achieve a weight of 83 g. The plate is gently placed on top of the specimen, such that the center point of the Plexiglas® plate is at least 40 mm away from any folds, with the entire plate resting on the specimen. A fold corresponds to a part of the absorbent article (e.g. the topsheet/acquisition web laminate) where the absorbent article has been folded for packaging purposes.

Two 50 mm×70 mm metal weights each having a mass of 1200 g (approximate thickness of 43 mm) are gently placed on the Plexiglas® plate such that a 70 mm edge of each metal weight is aligned with the 70 mm edges of the Plexiglas® plate. A metal frame having external dimensions of 70 mm×80 mm and interior dimensions of 42 mm×61 mm, and a total weight of 142 g (approximate thickness 6 mm), is positioned in the center of the Plexiglas® plate between the two end weights with the longest sides of the frame aligned with the longest sides of the plate.

If the specimen is smaller than 70×200 mm, or if a large enough area without a fold is not present, or if an area of interest is close to the edges of the specimen and can't be analyzed with the Plexiglas and weights settings described above, then the X-Y dimensions of the Plexiglas® plate and the added metal weights may be adjusted to reach a nominal external pressure of 1.86 kPa (0.27 psi) while maintaining a minimum 30×40 mm field of view. At least 10 complete three-dimensional protrusions of the specimen should be captured in the field of view of 30 mm×40 mm.

Position the projection head to be normal to the specimen surface (i.e. to the topsheet of the topsheet/acquisition web laminate).

Adjust the distance between the specimen and the projection head for best focus.

In the Primos Optical Profiler instrument, turn on the button "Pattern" to make a red cross appear on the screen cross and a black cross appears on the specimen.

Adjust the focus control until the black cross is aligned with the red cross on the screen.

Adjust image brightness then capture a digitized image.

In the Primos Optical Profiler instrument, change the aperture on the lens through the hole in the side of the projector head and/or altering the camera "gain" setting on the screen.

When the illumination is optimum, the red circle at the bottom of the screen labeled "I.O." will turn green.

Click on the "Measure" button.

The topology of the upper surface of the topsheet/acquisition web laminate specimen is measured through the Plexiglas plate over the entire field of view 30 mm×40 mm. It is important to keep the specimen still stationary during this time in order to avoid blurring of the captured image. The image should be captured within the 30 seconds following the placement of the Plexiglas plate, metal weights and frame on top of the specimen.

After the image has been captured, the X-Y-Z coordinates of every pixel of the 40 mm×30 mm field of view area are recorded. The X direction is the direction parallel to the longest edge of the rectangular field of view, the Y direction is the direction parallel to the shortest edge of the rectangular field of view. The Z direction is the direction perpendicular to the X-Y plane. The X-Y plane is horizontal while the Z direction is vertical, i.e. orthogonal to the X-Y plane.

These data are smoothed and filtered using a polynomial filter (n=6), a median filter 11 pixels by 11 pixels, and a structure filter 81 pixels by 81 pixels. The polynomial filter (n=6) approximates the X-Y-Z coordinate surface with a polynomial of order 6 and returns the difference to the approximated polynomial. The median filter 11 pixels by 11 pixels divides the field of view (40 mm×30 mm) in X-Y squares of 11 pixels by 11 pixels. The Z coordinate of the pixel located at the center of a given 11 pixels by 11 pixels square will be replaced by the mean Z value of all the pixels of this given square. The structure filter 81 pixels by 81 pixels, removes the waviness of the structure and translates all the Z peak values belonging to the bottom surface of the Plexiglas plate to a top X-Y plane.

A Reference Plane is then defined as the X-Y plane intercepting the surface topology profile of the entire field of view (i.e. 30 mm×40 mm), 100 microns below this top X-Y plane. In the Primos Optical Profiler instrument, to measure the Material Area of the Reference Plane (Z=−0.1 mm), click on the button "Evaluate". Then, apply a pre-filtering routine including a polynomial filter (n=6), a median filter 11 by 11 and a structure filter (n=81) using the function "Filter". Save the image to a computer file with ".omc" extension.

The same above procedure is then executed on the topsheet/acquisition web laminate with the garment-facing side upward (i.e. the acquisition web of the topsheet/acquisition web laminate being upward), the 40 mm×30 mm field of view being located at the exact same X-Y position of the topsheet/acquisition web laminate.

The Empty Area of the reference plane can be defined as the area of the Reference Plane that is above the surface profile. The Empty Areas having boundaries strictly located inside the field of view area (i.e. 30 mm×40 mm) without crossing or overlapping with the boundaries of the field of view area (i.e. 40 mm×30 mm) are defined as Isolated Empty Area(s). The Measured Protrusion Base Width is defined for an Isolated Empty Area as the diameter of the biggest circle that can be inscribed inside a given Isolated Empty Area. This circle should only overlap with the Isolated Empty Area.

In the Primos Optical Profiler instrument, this can be done by clicking on "Draw circle" and drawing the biggest inscribed circle possible in a chosen Isolated Empty Area. Click on "Show sectional picture", the circle diameter can be measure via clicking on the extremity of the sectional picture profile and then clicking on "Horizontal distance" to obtain the Protrusion Base Width.

For both of the acquired and digitized images, the Protrusion Base Width of all the Isolated Empty Areas is determined. Then, the Measured Protrusion Base Width is calculated as the arithmetic average of the 6 biggest Protrusion Base Widths.

3) Measured Protrusion Height Test Method

The topsheet/acquisition web laminate is extracted from the absorbent article as described above in the Measured Protrusion Base Width Test Method.

The topsheet/acquisition web laminate specimen comprising three-dimensional protrusions is then conditioned and scanned under a pressure of 1.86 kPa (0.27 psi) with the body-facing side upward, i.e. the topsheet of the topsheet/acquisition web laminate being upward as described above in the Measured Protrusion Base Width Test Method.

After the image has been captured, the X-Y-Z coordinates of every pixel of the 40 mm×30 mm field of view area are recorded and smoothed/filtered as described above in the Measured Protrusion Base Width Test Method. A reference plane is also defined as described above in the Measured Protrusion Base Width Test Method.

In the Primos Optical Profiler instrument, to measure the Material Area of the Reference Plane (Z=−0.1 mm), click on the button "Evaluate". Then apply a pre-filtering routine including a polynomial filter (n=6), a median filter 11 by 11 and a structure filter (n=81) using the function "Filter". Save the image to a computer file with ".omc" extension.

The same above procedure set out in the Measured Protrusion Base Width Test Method is then executed on the topsheet/acquisition web laminate with the garment-facing side upward (i.e. the acquisition web of the topsheet/acquisition web laminate being upward), the 40 mm×30 mm field of view being located at the exact same X-Y position of the topsheet/acquisition web laminate.

The Empty Area of the reference plane can be defined as the area of the Reference Plane that is above the surface profile. The Empty Area having boundaries strictly located inside the field of view area (i.e. 30 mm×40 mm) without crossing or overlapping with the boundaries of the field of view area (i.e. 40 mm×30 mm) are defined as Isolated Empty Area(s). The Protrusion Height is defined for an Isolated Empty Area as the distance between the minimum Z value of the points of the topsheet/acquisition web laminate surface profile having X-Y coordinates located in this Isolated Empty Area, and the Z value of the top X-Y plane.

Click on "Draw N parallel lines" and draw a first segment parallel to the X axis of the field of view (direction of the longest dimension of the field of view) passing through the center of the Isolated Empty Area and extending outside the Isolated Empty Area boundaries. The center of the Isolated Empty Area corresponds to the middle of the segment parallel to the Y axis of the field of view and joining the biggest and smallest Y value of the Isolated Empty Area. Then input the "number" of lines to be drawn and set the "distance" between lines to 0.05 mm. Enough lines need to be drawn such to cover the entire Isolated Empty Area. Leave the averaging parameter to 0 then click "Ok". Then click on "Show sectional picture". Click on the point of the sectional picture profile having the minimum Z value and click on "Vertical distance" to obtain the Protrusion Height.

For both of the acquired and digitized images, the Protrusion Height of all the Isolated Empty Areas is determined. Then, the Measured Protrusion Height is calculated as the arithmetic average of the 6 biggest Protrusion Heights.

Accelerated Compression Method

1. Cut 10 samples of the topsheet/acquisition web laminate 245 (called herein specimen) to be tested and 11 samples of paper towel into a 3 inch×3 inch (7.6 cm×7.6 cm) square.

2. Measure the caliper of each of the 10 specimens at 2.1 kPa and a dwell time of 2 seconds using a Thwing-Albert ProGage Thickness Tester or equivalent with a 50-60 millimeter diameter circular foot. Record the pre-compression caliper to the nearest 0.01 mm.

3. Alternate the layers of the specimens to be tested with the paper towels, starting and ending with the paper towels. The choice of paper towel does not matter and is present to prevent "nesting" of the protrusions in the deformed samples. The samples should be oriented so the edges of each of the specimens and each of the paper towels are relatively aligned, and the protrusions in the specimens are all oriented the same direction.

4. Place the stack of samples into a 40° C. oven and place a weight on top of the stack. The weight must be larger than the foot of the thickness tester. To simulate high pressures or low in-bag stack heights, apply 35 kPa (e.g. 17.5 kg weight over a 70×70 mm area). To simulate low pressures or high in-bag stack heights, apply 7 kPa (e.g. 3.5 kg weight over a 70×70 mm area).

5. Leave the samples in the oven for 15 hours. After the time period has elapsed, remove the weight from the samples and remove the samples from the oven.

6. Within 30 minutes of removing the samples from the oven, measure the post-compression caliper as directed in step 2 above, making sure to maintain the same order in which the pre-compression caliper was recorded. Record the post-compression caliper of each of the 10 specimens to the nearest 0.01 mm.

7. Let the samples rest at 23±2° C. and at 50±2% relative humidity for 24 hours without any weight on them.

8. After 24 hours, measure the post-recovery caliper of each of the 10 specimens as directed in step 2 above, making sure to maintain the same order in which the pre-compression and post-compression calipers were recorded. Record the post-recovery caliper of each of the 10 specimens to the nearest 0.01 mm. Calculate the amount of caliper recovery by subtracting the post-compression caliper from the post-recovery caliper and record to the nearest 0.01 mm.

9. If desired, an average of the 10 specimens can be calculated for the pre-compression, post-compression and post-recovery calipers.

Flat Acquisition Test Method

This method determines the acquisition times of a baby diaper. The method settings are depending on the diaper size tested. Table 1 shows commonly used diaper size descriptions to be used as reference.

TABLE 1

| commonly used size descriptions for diapers | | | |
|---|---|---|---|
| Size | Alternative Size Descriptions | | |
| 1 | newborn | | |
| 2 | S | P | Infant |
| 3 | M | | Crawler |
| 4 | L | G | Toddler |
| 5 | XL | XG | Walker |
| 6 | XXL | XXG | Junior |

Apparatus

Figure 10:
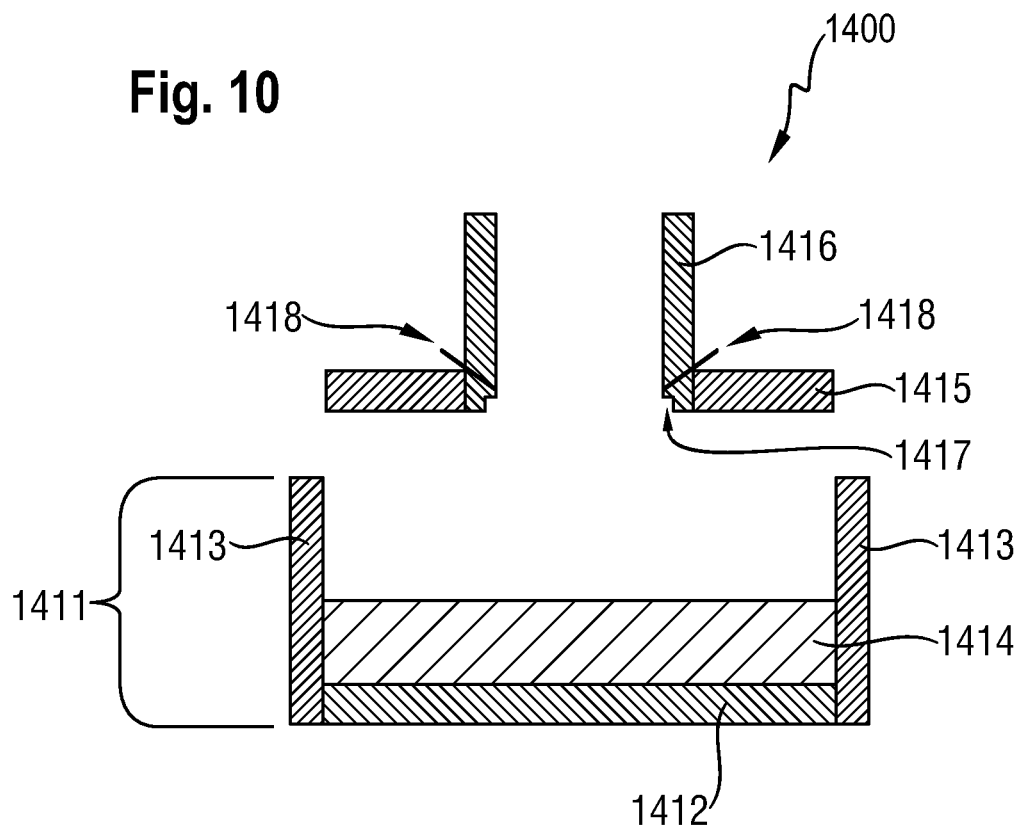
FIG. 10 shows an equipment assembly used in the Flat Acquisition Test Method.

The test apparatus 1400 is shown in FIG. 10 and comprises a trough 1411 made of polycarbonate (e.g. Lexan®) nominally 12.5 mm (0.5 inch) in thickness. The trough 1411 comprises a rectilinear horizontal base 1412 having a length of 508 mm (20.0 inches), and a width of 152 mm (6.0 inches). Two rectilinear vertical sides 1413, 64 mm (2.5 inches) tall×508 mm (20 inches) in length are affixed to the long edges of the base 1412 to form a U-shaped trough 1411 having a length of 508 mm (20.0 inches), an internal width of 152 mm (6.0 inches), and an internal depth of 51 mm (2.0 inches). The front and back ends of the trough 1411 are not enclosed.

A slab of open-cell polyurethane foam 1414 with dimensions 508×152×25 mm is wrapped in polyethylene film and placed in the bottom of the trough 1411 in such a way that the edges of the foam 1414 and the trough 1411 are aligned, and the upper surface of the polyethylene film is smooth and free of seams, wrinkles or imperfections. The polyurethane foam 1414 has a compression hardness at 40% compression $CV_{40}$ of 2.4 kPa+/−0.4 kPa as determined according to DIN EN ISO 3386 and a density of 16 kg/m$^3$+/−2 kg/m$^3$ as determined according to DIN EN ISO 845, e.g. a film wrapped foam can be purchased from Crossroads Machine Inc., Englewood Ohio 45322, USA under the description of "FOAM BASE FOR LIQUID ACQUISITION TEST", or equivalent film-wrapped foam may be used. A reference line is drawn across the width of the upper surface of the polyethylene cover 121 mm (6.0 inches) from one end (the front edge) parallel to the transverse centerline using an indelible marker: such reference line distance must be adjusted according to size based on the table 1.

A rectilinear polycarbonate top plate 1415 has a nominal thickness of 12.5 mm (0.5 inch), a length of 508 mm (20.0 inches), and a width of 146 mm (5.75 inches). A 51 mm (2.0 inch) diameter hole is bored in the center of the top plate 1415 (i.e. the center of the hole is located at the intersection of the longitudinal and transverse axes of the upper surface of the top plate 1415). A polycarbonate cylinder 1416 with an outside diameter of 51 mm (2.0 inches), an internal diameter of 37.5 mm (1.5 inches) and a height of 102 mm (4.0 inches) is glued into the hole in the top plate 1415 so that the bottom edge of the cylinder 1416 is flush with the lower surface of the top plate 1415 and the cylinder 1416 protrudes vertically 89 mm (3.5 inches) above the upper surface of the top plate 1415, and the seam between the cylinder 1416 and the top plate 1415 is watertight. An annular recess 1417 with a height of 2 mm (0.08 inch) and a diameter of 44.5 mm (1.75 inches) is machined into the bottom internal edge of the cylinder 1416. A nylon wire mesh (the opening of this nylon mesh is 1.5 mm, the nylon wire diameter is 0.5 mm) is glued into the recess 1417. The mesh is prepared via cutting a circle of 44.5 mm diameter and cutting of 5 mm of the diameter at each opposite side (i.e. 180° apart). Two 1 mm diameter holes are drilled at a 45° angle to the upper surface of the top plate 1415 so that the holes intersect the inner surface of the cylinder 1416 immediately above the recess 1417 and are at opposite sides of the cylinder 1416 (i.e. 180° apart). Two stainless steel wires 1418 having a diameter of 1 mm are glued into the holes in a watertight fashion so that one end of each wire is flush with the inner cylinder wall and the other end protrudes from the upper surface of the top plate 1415. These wires are referred to as electrodes herein below. A reference line is scribed across the width of the top plate 1415 at a specific distance from the front edge parallel to the transverse centerline. The distance is size specific and shown in table 2 below. For example 121 mm is the distance for size 4. The top plate 1415/cylinder 1416 assembly has a weight of approximately 1180 grams.

TABLE 2

Size specific distances, gush volumes and rates

| Size | Reference line distance [mm] | Gush volume [ml] | Gush rate [ml/s] |
|---|---|---|---|
| 1 | 160 | 24 | 8 |
| 2 | 147 | 40 | 8 |
| 3 | 134 | 50 | 10 |
| 4 | 121 | 75 | 15 |
| 5 | 121 | 75 | 15 |
| 6 | 121 | 75 | 15 |

Two steel weights each weighing 4.5 Kg and measuring 146 mm (5.75 inches) wide, 38 mm (1.5 inches) deep, and approximately 100 mm (4 inches tall) are also required.

Procedure

All testing is carried out at 23±2° C. and 50±10% relative humidity.

The polycarbonate trough 1411 containing the wrapped foam slab 1414 is placed on a suitable flat horizontal surface. A disposable absorbent product is removed from its packaging and the cuff elastics are cut at suitable intervals to allow the product to lay flat. The product is weighed to within ±0.1 grams on a suitable top-loading balance then placed on the covered foam slab 1414 in the acquisition apparatus with the front waist edge of the product aligned with the reference mark on the polyethylene cover. The product is centered along the longitudinal centerline of the apparatus with the topsheet (body-side) of the product facing upwards and the rear waist edge toward the rear end of the foam slab 1414. The top plate 1415 is placed on top of the product with the protruding cylinder facing upwards. The scribed reference line is aligned with the front waist edge of the product and the rear end of the top plate 1415 is aligned with the rear edge of the foam slab 1414. The two 4.5 Kg weights are then gently placed onto the top plate 1415 so that the width of each weight is parallel to the transverse centerline of the top plate, and each weight is 83 mm (3.25 inches) from the front or rear edge of the top plate 1415. The point of the topsheet of the product falling at the center of the cylinder is marked as loading point of the article.

A suitable electrical circuit is connected to the two electrodes to detect the presence of an electrically conductive fluid between them.

A suitable pump; e.g. Model 7520-00 supplied by Cole Parmer Instruments, Chicago, USA, or equivalent; is set up to discharge a 0.9 mass % aqueous solution of sodium chloride through a flexible plastic tube having an internal diameter of 4.8 mm (3/16 inch), e.g. Tygon® R-3603 or equivalent. The end portion of the tube is clamped vertically so that it is centered within the cylinder 1416 attached to the top plate 1415 with the discharge end of the tube facing downwards and located 50 mm (2 inches) below the upper edge of the cylinder 1416. The pump is operated via a timer and is pre-calibrated to discharge a gush of 75.0 ml of the 0.9% saline solution at a rate of 15 ml/sec (for size 4 or equivalent). The volume and rate to be used for specific sizes is illustrated in the table 1 above.

In the following the case of size 4 is exemplified: for other sizes the only difference will be to replace the reference line distance, gush volume and gush rate for the specific size as defined in the table 1. The pump is activated and a timer started immediately upon activation. The pump delivers 75 mL of 0.9% NaCl solution to the cylinder 1416 at a rate of 15 ml/sec, then stops. As test fluid is introduced to the cylinder 1416, it typically builds up on top of the absorbent structure to some extent. This fluid completes an electrical circuit between the two electrodes in the cylinder. After the gush has been delivered, the meniscus of the solution drops as the fluid is absorbed into the structure. When the electrical circuit is broken due to the absence of free fluid between the electrodes in the cylinder, the time is noted.

The acquisition time for a particular gush is the time interval between activation of the pump for that gush, and the point at which the electrical circuit is broken.

Four gushes are delivered to the product in this fashion; each gush is 75 ml and is delivered at 15 ml/sec. The time interval between the end of a certain gush, i.e. when the electrical circuit is broken after the liquid acquisition, and the beginning of the next gush is 300 seconds.

The acquisition time for four gushes is recorded to the nearest 1.0 s. Eight products for each option are tested in this fashion and the average gush time for each of the respective gushes (first through fourth) is calculated.

A new foam base 1414 is taken for each test or let the foam base relax for at least 24 hours before re-using it.

The total acquisition time is the sum of the acquisition time of gush 1, the acquisition time of gush 2, the acquisition time of gush 3 and the acquisition time of gush 4. The total acquisition time is expressed in seconds.

Liquid in Topsheet Test Method

Objective

The Liquid in topsheet Test Method is the determination of the retained liquid in the topsheet, i.e. a measure of the topsheet dryness. In order to determine the amount of residual fluid in the topsheet, i.e. the liquid in topsheet, it is aimed at measuring the wet topsheet sample weight, i.e. after removing from the diaper test sample and separating from the acquisition web, and dry the topsheet sample weight after at least 16 hours in an oven at 60° C.

Experiment Setup

Mark the loading point of the diaper as it has been described in the Flat acquisition test method as set out above.

Take the diaper out of the Flat Acquisition Test Method apparatus.

On the diaper, when the topsheet is facing the operator, mark using a permanent ink pen and a plexiglass template (55 mm wide in cross direction, 120 mm long in machine direction, 1-5 mm thick) a rectangle onto the topsheet, symmetrically (centered in cross direction and machine direction) around the loading point.

Perform the Flat acquisition test method as described above.

At least 10 minutes, but not more than 11 minutes after the last gush of the above acquisition test is absorbed, remove the cover plate and weights, and Place carefully the diaper test sample flat on a lab bench.

Preparation of the wet topsheet sample and determination of the Liquid in topsheet The topsheet/acquisition web laminate is then cut with a scalpel along the marked rectangle.

The wet topsheet of the topsheet/acquisition web laminate is carefully separated from the acquisition web underneath while touching it only with tweezers and as little as possible: if necessary freeze off spray can be used to remove more easily the topsheet without tearing it. The wet topsheet sample has dimensions of 55 mm wide and 120 mm long.

The wet topsheet sample is put in a tarred Petri dish.

Then, the wet topsheet sample is weighed to the nearest 0.001 g, which provides the wet topsheet sample weight.

The wet topsheet sample, contained in its Petri dish, is placed for at least 16 hours into an oven at 60° C.

Then, the Petri dish with the topsheet sample is taken out of the oven; let it cool down to the controlled environment of the test room for at least 10 minutes.

The dry topsheet sample is placed on a new tarred Petri dish. The weight of the dry topsheet sample is recorded from a balance to the nearest 0.001 g.

The liquid in topsheet is then calculated as the difference between the wet topsheet sample and dry topsheet sample weights.

Four samples for each type of absorbent article are tested according to this procedure and the average liquid in topsheet is calculated.

The topsheet load is calculated as the ratio of the liquid in topsheet with the weight of the dry topsheet. Four samples for each type of absorbent article are tested according to this procedure and the average topsheet load is calculated.

Opacity Test Method:

Opacity is a measure of the capacity of a material to obscure the background behind it. The value for opacity is obtained by dividing the reflectance obtained with a black backing (RB) for the material, by the reflectance obtained for the same material with a white background (WB). This is called the contrast ratio (CR) method.

$$\% \text{ Opacity} = \frac{RB}{RW} \times 100$$

Using a Hunter Colorimeter set to XYZ color scale, opacity is defined as:

$$\% \text{ Opacity} = \frac{Y \text{ reading over black plate}}{Y \text{ reading over white plate}} \times 100$$

Sample Preparation

A specimen of suitable size (generally about 10 cm square) is cut for analysis. The specimen must be free of creases, wrinkles, tears and other obvious defects.

If the opacity of the material is affected by temperature and/or humidity, the specimens must be conditioned under standard conditions (23° C.+/−2° C. and 50%+/−10% Relative Humidity) until equilibrium is reached, and measured under those conditions.

If the topsheet material is treated with one or more surfactants, the material used for the test is the surfactant-treated topsheet material.

Equipment

Hunter Labscan® XE available from Hunter Associates Laboratory, Inc., USA. The instrument is configured as follows:

Geometry 45°/0°

Color Scale XYZ

Illuminant D65

Observer 10°

The colorimeter is calibrated using the standard gloss black glass and gloss white tile supplied with the instrument according to the manufacturer's instructions.

Test Procedure

The specimen is placed on the white tile and inserted into the colorimeter according to the manufacturer's instructions. The machine direction of the specimen should be aligned front-to-back in the instrument. The Y reading is recorded to the nearest 0.1 unit. The procedure is repeated using the black standard plate instead of the white standard tile.

Ten specimens are measured and the opacity results are averaged to obtain the % opacity value for the material.

$$\% \text{ Opacity} = \frac{\text{``}Y\text{'' on black plate}}{\text{``}Y\text{'' on white plate}} \times 100$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene comprising:
a longitudinal axis;
a transversal axis perpendicular to the longitudinal axis;
a topsheet/acquisition web laminate;
a liquid impermeable backsheet; and
an absorbent core, wherein the absorbent core is located at least partially between the topsheet/acquisition web laminate and the backsheet;
wherein the topsheet/acquisition web laminate comprises a liquid permeable topsheet and an acquisition web in a face to face relationship, wherein the topsheet/acquisition web laminate comprises three-dimensional protrusions extending from a plane of the topsheet/acquisition web laminate;
wherein the acquisition web is a nonwoven fibrous web comprising an upper layer facing towards the topsheet and a lower layer facing towards the absorbent core, wherein the average diameter of the fibers in the upper layer is higher than the average diameter of the fibers in the lower layer, wherein the lower layer of the acquisition web comprises from about 60% to about 80% of a first type of fibers and from about 20% to about 40% of a second type of fibers, or the lower layer of the acquisition web comprises from about 60% to about 70% of a first type of fibers and from about 30% to about 40% of a second type of fibers.

2. The absorbent article according to claim 1, wherein the acquisition web is a carded nonwoven fibrous web.

3. The absorbent article according to claim 1, wherein the lower layer comprises a mixture of a first type of fibers having a diameter from about 3.5 to about 10 denier and of a second type of fibers having a diameter from about 0.8 to about 2.5 denier.

4. The absorbent article according to claim 3, wherein the first type of fibers of the lower layer of the acquisition web are multicomponent fibers, and wherein the multicomponent fibers are core/sheath bicomponent fibers.

5. The absorbent article according to claim 3, wherein the second type of fibers of the lower layer of the acquisition web are monocomponent fibers, and wherein the monocomponent fibers are trilobal monocomponent fibers.

6. The absorbent article according to claim 1, wherein the diameter of the fibers of the upper layer is from about 3.5 to about 10 denier.

7. The absorbent article according to claim 1, wherein the diameter of the fibers of the upper layer is from about 4 to about 8 denier.

8. The absorbent article according to claim 1, wherein the ratio of the weight of the upper layer compared to the weight of the lower layer ranges from about 1:4 to about 2.5:1.

9. The absorbent article according to claim 1, wherein the ratio of the weight of the upper layer compared to the weight of the lower layer ranges from about 1:2.5 to about 2:1.

10. The absorbent article according to claim 1, wherein the ratio of the weight of the upper layer compared to the weight of the lower layer ranges from about 1:2 to about 1:1.

11. The absorbent article according to claim 1, wherein the acquisition web of the topsheet/acquisition web laminate comprises synthetic fibers made of polypropylene, polyethylene, polyester, polyethylene terephthalate, polybutylene terephthalate, polyamide, and combinations thereof.

12. The absorbent article according to claim 1, wherein the upper layer of the acquisition web comprises multicomponent fibers, and wherein the multicomponent fibers are core/sheath bicomponent fibers.

13. The absorbent article according to claim 1, wherein the fibers of the acquisition web are autogenously bonded.

14. The absorbent article according to claim 1, wherein the majority of the three-dimensional protrusions of the topsheet/acquisition web laminate protrude generally towards the backsheet of the absorbent article.

15. The absorbent article according to claim 1, wherein the topsheet/acquisition web laminate has a liquid in topsheet value of less than 200 mg, or less than 180 mg, according to the Liquid in Topsheet test method.

16. The absorbent article according to claim 1, wherein the three-dimensional protrusions are formed from the fibers of the topsheet and the acquisition web, wherein a majority of the three-dimensional protrusions each comprise a base forming an opening, an opposed distal portion and one or more side walls between the base and the distal portion, wherein the base, the distal portion, and the one or more side walls are formed by fibers such that the majority of the three-dimensional protrusions have openings at the base.

17. The absorbent article according to claim 1, wherein the absorbent core comprises an absorbent material, and wherein the absorbent material comprises from about 80% to about 100% of superabsorbent polymers by total weight of the absorbent material.

18. The absorbent article according to claim 1, wherein a width of the acquisition web in a direction parallel to the transversal axis is less than a width of the topsheet in a direction parallel to the transversal axis of the absorbent article.

19. An absorbent article for personal hygiene comprising:
a longitudinal axis;
a transversal axis perpendicular to the longitudinal axis;
a topsheet/acquisition web laminate;
a liquid impermeable backsheet; and
an absorbent core, wherein the absorbent core is located at least partially between the topsheet/acquisition web laminate and the backsheet;
wherein the topsheet/acquisition web laminate comprises a liquid permeable topsheet and an acquisition web in a face to face relationship, wherein the topsheet/acquisition web laminate comprises three-dimensional protrusions extending from a plane of the topsheet/acquisition web laminate, wherein the acquisition web is a nonwoven fibrous web comprising an upper layer facing towards the topsheet and a lower layer facing towards the absorbent core, wherein the average diameter of the fibers in the upper layer is higher than the average diameter of the fibers in the lower layer, wherein the lower layer comprises a mixture of a first type of fibers having a diameter from about 3.5 to about 10 denier and of a second type of fibers having a diameter from about 0.8 to about 2.5 denier, and wherein the first type of fibers of the lower layer of the acquisition web are multicomponent fibers, and wherein the multicomponent fibers are core/sheath bicomponent fibers.

20. An absorbent article for personal hygiene comprising:
a longitudinal axis;
a transversal axis perpendicular to the longitudinal axis;
a topsheet/acquisition web laminate;
a liquid impermeable backsheet; and an absorbent core, wherein the absorbent core is located at least partially between the topsheet/acquisition web laminate and the backsheet, wherein the topsheet/acquisition web laminate comprises a liquid permeable topsheet and an acquisition web in a face to face relationship, wherein the topsheet/acquisition web laminate comprises three-dimensional protrusions extending from a plane of the topsheet/acquisition web laminate, wherein the acquisition web is a nonwoven fibrous web comprising an upper layer facing towards the topsheet and a lower layer facing towards the absorbent core, wherein the average diameter of the fibers in the upper layer is higher than the average diameter of the fibers in the lower layer, wherein the lower layer comprises a mixture of a first type of fibers having a diameter from about 3.5 to about 10 denier and of a second type of fibers having a diameter from about 0.8 to about 2.5 denier, and wherein the second type of fibers of the lower layer of the acquisition web are monocomponent fibers, and wherein the monocomponent fibers are trilobal monocomponent fibers.

* * * * *